US008557547B2

(12) United States Patent
Horne et al.

(10) Patent No.: US 8,557,547 B2
(45) Date of Patent: *Oct. 15, 2013

(54) PHOSPHOTRIESTERASE FROM AGROBACTERIUM RADIOBACTER P230

(71) Applicant: Commonwealth Scientific and Industrial Research Organisation, Campbell (AU)

(72) Inventors: Irene Horne, Yass (AU); Tara Sutherland, Watson (AU); Rebecca Harcourt, North Ryde (AU); Robyn Russell, Wanniassa (AU); John Oakeshott, Wanniassa (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/651,250

(22) Filed: Oct. 12, 2012

(65) Prior Publication Data

US 2013/0040367 A1 Feb. 14, 2013

Related U.S. Application Data

(62) Division of application No. 10/477,469, filed as application No. PCT/AU02/00594 on May 15, 2002, now Pat. No. 8,293,244.

(30) Foreign Application Priority Data

May 15, 2001 (AU) ...................................... PR5023

(51) Int. Cl.
*C12P 21/04* (2006.01)
(52) U.S. Cl.
USPC ...... 435/71.1; 435/69.1; 435/320.1; 435/243; 435/252.3; 536/23.7; 530/350
(58) Field of Classification Search
None
See application file for complete search history.

(56) References Cited

U.S. PATENT DOCUMENTS

| | | | |
|---|---|---|---|
| 5,484,728 A | 1/1996 | Serdar et al. | |
| 5,589,386 A | 12/1996 | Serdar | |
| 5,756,671 A | 5/1998 | Gyuris et al. | |
| 6,469,145 B1 | 10/2002 | Rastogi et al. | |
| 6,498,235 B2 | 12/2002 | Sheppard et al. | |
| 6,943,234 B2 | 9/2005 | Raymond et al. | |
| 7,396,980 B2 | 7/2008 | Simmons et al. | |
| 7,485,715 B2 | 2/2009 | Alexandrov et al. | |
| 7,638,602 B2 | 12/2009 | Presnell et al. | |
| 8,293,244 B2 * | 10/2012 | Horne et al. | 424/190.1 |
| 2004/0161818 A1 | 8/2004 | Horne et al. | |

FOREIGN PATENT DOCUMENTS

| | | |
|---|---|---|
| WO | WO 90/02177 | 3/1990 |
| WO | WO 95/19440 A1 | 7/1995 |
| WO | WO 97/19176 A1 | 5/1997 |
| WO | WO 99/53037 A2 | 10/1999 |
| WO | WO 00/64539 | 11/2000 |
| WO | WO 00/65081 | 11/2000 |

OTHER PUBLICATIONS

Banzone, J. A. et al., (1995) "Histidine-254 is essential for the inactivation of phosphotriesterase with the alkynyl phosphate esters and diethyl pyrocarbohate," Biochemistry 34:750-754.
Benning, M. M. et al., (1994) "Three-dimensional structure of phosphotriesterase: An enzyme capable of detoxifying organophosphate nerve agents," Biochemistry 33:15001-15007.
Benning, M.M. et al. (1995) "Three-Dimensional Structure of the Binuclear Metal Center for Phosphotriesterase"; Biochemistry 34:7973-7978.
Benning, M.M. et al. (2000) "The Binding of Substrate Analogs to Phosphotriesterase"; J. Biol. Chem. 275(39):30556-30560.
Benning, M.M. et al., (2001) "High resolution x-ray structures of different metal-substituted forms of phosphotriesterase from *Pseudomonas diminuta*," Biochemistry 40:2712-2722.
Billecke, 5.5. et al. (1999) "Characterization of a soluble mouse liver enzyme capable of hydrolyzing diisopropyl phosphorofluoridate"; Chem. Biol. Interact. 119-120:251-256.
Broomfield, C.A. et al. (1999) "Protein engineering of a human enzyme that hydrolyzes V and G nerve agents: design, construction and characterization"; Chem. Biol. Interact. 119-120:413-418.
Buchbinder, J.L. et al. (1998) "Biochemical Characterization and Crystallographic Structure of an *Escherichia coil* Protein from the Phosphotriesterase Gene Family"; Biochemistry 37:5096-5160.
Caldwell, S. R. et al., (1991) "Limits of diffusion in the hydrolysis of substrates by the phosphotriesterase from *Pseudomonas diminuta*," Biochemistry 30:7438-7444.
Campbell, P.M. et al. (1998) "Two different amino acid substitutions in the ali-esterase, E3, confer alternative types of organophosphorus insecticide resistance in the sheep blowfly, *Lucilia cuprina*"; Insect Biochemistry and Molecular Biology 28: 139-150.
Chen-Goodspeed, M. et al., (2001) "Structural determinants of the substrate and stereochemical specificity of phosphotriesterase," Biochemistry 40: 1325-1331.
Chen-Goodspeed, M. et al., (2001) "Enhancement, relaxation, and reversal of the stereoselectivity for phosphotriesterase by rational evolution of active site residues," Biochemistry 40: 1332-1339.

(Continued)

*Primary Examiner* — Jennifer Graser
(74) *Attorney, Agent, or Firm* — John P. White; Gary J. Gershik; Cooper & Dunham LLP

(57) ABSTRACT

The present invention provides enzymes capable of hydrolysing organophosphate (OP) molecules. In particular, the invention provides a phosphotriesterase enzyme identified from an *Agrobacterium radiobacter* strain isolated from soil that hydrolyses OP pesticides, and the gene encoding that enzyme. The invention also provides mutants of the identified phosphotriesterase enzyme which have altered substrate specificity. The use of these enzymes in bioremediation strategies is also provided.

21 Claims, 4 Drawing Sheets

(56) References Cited

OTHER PUBLICATIONS

Cheng, T. et al. (1999) "*Alteromonas prolidase* for organophosphorus G-agent decontamination"; Chem. Biol. Interact. 119-120:455-462.

Cho, C.M.-H. et al., (2002) "Bacterial cell surface display of organophosphorus hydrolase for selective screening of improved hydrolysis of organophosphate nerve agents," Applied and Environmental Microbiology 68(4):2026-2030.

Claudianos, C. et al. (1999) "The same amino acid substitution in orthologous esterases confers organophosphate resistance on the house fly and a blowfly"; Insect Biochemistry and Molecular Biology 29:675-686.

Cook, A.M. et al. (1978) "Phosphorus-Containing Pesticide Breakdown Products: Quantitative Utilization as Phosphorus Sources by Bacteria"; Applied and Environ. Microbiol. 36(5):668-672.

Davies, J.A. et al. (1997) "Molecular cloning and expression pattern of rpr-1, A resiniferatoxin-binding, phosphotriesterase-related protein, expressed in rat kidney tubules"; FEBS Letters 410:378-382.

diSoudi, B. et al. (1999) "Modification of Near Active Site Residues in Organophosphorus Hydrolase Reduces Metal Stoichiometry and Alters Substrate Specificity"; Biochemistry 38:2866-2872.

DiSioudi, B. D. et al., (1999) "Rational design of organophosphorus hydrolase for altered substrate specificities," Chemico-Biological Interactions 119-120:211,223.

Donarski, W. J. et al., (1989) "Structure-activity relationships in the hydrolysis of substrates by the phosphotriesterase from *Pseudomonas diminuta*," Biochemistry 28:4650-4655.

Doorn, J.A. (1999) "Evidence that several conserved histidine residues are required for hydrolytic activity of human paraoxonase/aryiesterase"; Chem. Biol. Interact. 120:235-241.

Dumas, D. P. et al. (1989) "Purification and Properties of the Phosphotriesterase from *Pseudomonas diminuta*"; J. Biol. Chem. 264:19659-19665.

Dumas, D.P. et al. (1990) "Expression of *Pseudomonas phosphotriesterase* activity in the fall armyworm confers resistance to insecticides"; Experientia 46:729-731.

Dumas, D.P. at al. (1989) "Diisopropylfluorophosphate Hydrolysis by a Phosphotriesterase from *Pseudomonas diminuta*"; Biotechnol. Appl. Biochem. 11 :235-243.

Elashvili, I. et al. (1998) "*phnE* and *glpT* Genes Enhance Utilization of Organophosphates in *Escherichia coli* K-12"; Applied and Environ. Microbiol. 64(7):2601-2608.

Gan, K.N. et al. (1991) "Purification of Human Serum Paraoxonase/Arylesterase: Evidence for One Esterase Catalyzing Both Activities"; Drug Metabolism and Disposition 19(1):100-106.

Gardiner, A.T. et al. (1996) "The purple photosynthetic bacterium *Rhodopseudomonas acidophila* contains multiple *puc* peripheral antenna complex (LH2) genes: Cloning and initial characterisation of four β/α pairs" Photosyn. Res. 49:223-2235.

Ghisalba, O. et al. (1987) "Microbial degradation and utilization of selected organophosphorus compounds—stragegies and applications," CHIMIA 41 (6):206-215.

Gopal, S. et al., (2000) "Mutagenesis of organophosphorus hydrolase to enhance hydrolysis of the nerve agent VX," Biochemical and Biophysical Research Communications 279:516-519.

Grimsley, J. K. et al., (1997) "Organophosphorus hydrolase is a remarkably stable enzyme that unfolds through a homodirneric intermediate," Biochemistry 36:14366-14374.

Harcourt, R.L. et al. (2002) "Development of a simple and sensitive fluorimetric method for isolation of coumaphos-hydrolysing bacteria"; Letters in Appl. Microbiol. 34:263-268.

Harel, M. et al. (1992) "Conversion of acetylcholinesterase to butyrylcholinesterase: Modeling and mutagenesis," Proc. Natl. Acad. Sci. USA 89:10827-10831.

Harper, L.L. et al. (1988) "Dissimilar Plasmids Isolated from *Pseudomonas diminuta* MG and a *Flavobacterium* sp. (ATCC 27551) Contain Identical *opd* Genes"; Applied and Environmental Microbiology 54:2586-2589.

Havens, P.L. et al. "Reusable Immobilized Enzyme/Polyurethane Sponge for Removal and Detoxification of Localized Organophosphate Pesticide Spills"; Industrial & Engineering Chemistry Research, American Chemical Society, Washington, U.S. (1993) 32:2254-2258.

Hong, S.-B. et al., (1996) "Metal-substrate interactions facilitate the catalytic activity of the bacterial phosphotriesterase," Biochemistry 35: 10904-1 0912.

Hong, S.B. et al. (1999) "Stereochemical preferences for chiral substrates by the bacterial phosphotriesterase"; Chem. Biol. Interact. 120:225-234.

Hong, S.-B. et al., (1999) "Stereochemical constraints on the substrate specificity of phosphotriesterase," Biochemistry 38: 1159-1165.

Horne, I. et al. "Identification of an *opd* (Organophosphate Degradation) Gene in an *Agrobacterium* Isolate"; Applied and Environmental Microbiology (Jul. 2002) 68(7):3371-3376.

Hoskin, F.C.C. et al. (1999) "Organophosphorus acid anhydrolase in slime mold duckweek and mung bean: A continuing search for a physiological role and a natural substrate"; Chem. Biol. Interact. 120:399-404.

Ibrahim, F.B. et al. (1966) "Ultraviolet Spectrophotometric Method for Fenthion"; J. Agr. Food Chem. 14(4):369-371.

Jackson, C. J. et al., (2009) "Structure-based rational design of a phosphotriesterase," Applied and Environmental Macrobiology 75(15):5153-5156.

Kuo, J. M. et al., (1994) "Identification of the histidine ligands to the binuclear metal center of phosphotriesterase by site-directed mutagenesis," Biochemistry 33:4265-4272.

Kuo, J. M. et al., (1997) "Perturbations to the active site of phosphotriesterase," Biochemistry 36:1982-1988.

Lai, K. et al. (1995) "Characterization of P-S Bond Hydrolysis in Organophosphorothioate Pesticides by Organophosphorus Hydrolase"; Archives of Biochem. and Biophysics 318:59-64.

LeJeune, K.E. et al. (1998) "Nerve agents degraded by enzymatic foams"; Nature 395:27-28.

Li, W.-S. et al., (2001) "Stereoselective detoxification of chiral sarin and soman analogues by phosphotriesterase," Bioorganic & Medicinal Chemistry 9:2083-2091.

Liu, W. et al., (1992) "Enhancement of the chemical and antimicrobial properties of subtilin by site-directed mutagenesis," Journal of Biological Chemistry 267(35):25078-25085.

McAuliffe, K. S. et al., (1990) "Glyphosate degradation by *Agrobacterium radiobacter* isolated from activated sludge," J Industrial Microbiology 6:219-221.

Muh, U. et al., (1994) "Lactate monooxygenase. I. Expression of the mycobacterial gene in *Escherichia coil* and site-directed mutagenesis of lysine 266," Journal of Biological Chemistry 269(11):7982-7988.

Mulbry, W.W. (1992) "The aryldialkylphosphatase-encoding gene adpB from *Nocardia* sp. strain B-1: cloning, sequencing and expression in *Escherichia coli*"; Gene 121:149-153.

Mulbry, W.W. et al. (1989) "Parathion Hydrolase Specified by the *Flavobacterium opd* Gene: Relationship between the Gene and Protein"; J. of Bact. 171(12):6740-6746.

Mulbry, W.W. et al. (1991) "Degradation of pesticides by microorganisms and the potential for genetic manipulation"; Crop Protection 10:334-345.

Munnecke, D.M. et al. (1976) "Pathways of Microbial Metabolism of Parathion"; Applied & Environ. Microbiol. 31(1):63-69.

Newcomb, R.D. et al. (1997) "A single amino acid substitution coverts a carboxylesterase to an organophosphorus hydrolase and confers insecticide resistance on a blowfly"; Proc. Nat. Acad. Sci. USA 94:7464-7468.

Raushel, F. M., (2002) "Bacterial detoxification of organophosphate nerve agents," Current Opinion in Microbiology 5:288-295.

Rekha, K. et al. (2000) "Biosensors for the Detection of Organophosphorous Pesticides"; Biotechnology 20(3):213-235.

Rosenberg, A. et al. (1979) "Microbial Cleavage of Various Organophosphorus Insecticides"; Applied & Environ. Microbiol. 37(5):886-891.

Roth, M. (1969) "Fluorimetric Assay of Enzymes"; Methods of Biochemical Analysis 17:189-285.

Scanlan, T.S. et al. (1995) "Evolution in Action"; Chem. and Biol. 2(2):71-75.

(56) References Cited

OTHER PUBLICATIONS

Schwede, T. et al., (2003) "Swiss-Model: An automated protein homology-modeling server," Nucleic Acids Research 31 (13):3381-3385.
Serdar, C.M. et al. (1989) "Parathion hydrolase gene from *Pseudomonas diminuta* MG: subcloning, complete nucleotide sequence, and expression of the mature portion of the enzyme in *Escherichia coli*"; Biotechnology 7: 1151-1155.
Shim, H. et al., (1998) "Hydrolysis of phosphodiesters through transformation of the bacterial phosphotriesterase," Journal of Biological Chemistry 273 (28) :17445-17450.
Shim, H. et al., (2000) "Self-assembly of the binuclear metal center of phosphotriesterase," Biochemistry 39:7357-7364.
Simon, I. et al., (2001) "Predicting protein conformation by statistical methods," Biochimica et Biophysica Acta 1549:123-136.
Sorenson, R.C. et al. (1995) "Reconsideration of the catalytic center and mechanism of mammalian paraoxonase/arylesterase"; Proc. Nat. Acad. Sci. USA 92:7187-7191.
Sogorb, M.A. and Vilanova, E., (2002) "Enzymes involved in the detoxification of organophosphorus, carbamate and pyrethroid insecticides through hydrolysis," Toxicology Letters 128:215-228.
Vanhooke, J. L. et al., (1996) "Three-dimensional structure of the zinc-containing phosphotriesterase with the bound substrate analog diethyl 4-methylbenzylphosphonate," Biochemistry 35:6020-6025.
Wackett, L. P. et al., (1987) Bacterial carbon-phosphorus lyase: Products, rates, and regulation of phosphonic and phosphinic acid metabolism, J Bacteriology 169(2):710-717.
Wang, Q. et al. (1998) "Purification and Properties of Soman-Hydrolyzing Enzyme from Human Liver"; J. Biochem. and Molecular Toxicology 12(4):213-217.
Wang, F. et al. (1993) "Purification and Properties of a Diisopropyl-Fluorophosphatase from Squid *Todarodes pacificus* Steenstrup"; J. Biochern. Toxicology 8(3):161-166.
Watkins, L. M. et al. (1997) "Augmented hydrolysis of diisopropyl fluorophosphate in engineered mutant of phosphotriesterase," Journal of Biological Chemistry 272(41):25596-25601.
Wu, F. et al., (2000) "Rationally engineered mutants of phosphotriesterase for preparative scale isolation of chiral organophosphates," J. Am. Chem. Soc. 122:10206-10207.
Yang, F. et al. (1995) "Nonaqueous Biocatalytic Degradation of a Nerve Gas Mimic"; Biotechnol. Prog. 11:471-474.
Zimmerer, R.P. et al. (1996) "Isolation and Morphology of Temperate *Agrobacterium tumefaciens* Bacteriophage"; J. Bacteriol. 92(3):746-750.
First Examination Report, issued Jun. 18, 2008 in connection with European Patent Application No. 02721861.9.
Second Examination Report, issued Feb. 3, 2009 in connection with European Patent Application No. 02721861.9.
Third Examination Report, issued Nov. 11, 2009 in connection with European Patent Application No. 02721861.9.
Response to First Examination Report, filed Dec. 3, 2008 in connection with corresponding European Patent Application No. 02721861.9.
Response to Second Examination Report, filed Aug. 6, 2009 in connection with European Patent Application No. 02721861.9.
Response to Third Examination Report, filed Feb. 18, 2010 in connection with European Patent Application No. 02721861.9.
Bowie et al., (1990) "Deciphering the message in protein sequences: tolerance to amino acid substitutions" Science 257:1306-1310.
Greenspan et al., (1999) "Defining epitopes: It's not as easy as it seems" Nature Biotechnology 7:936-937.
Dec. 22, 2006 Office Action, issued in connection with U.S. Appl. No. 10/477,469.
Mar. 6, 2007 Response to Office Action, filed in connection with U.S. Appl. No. 10/477,469.
May 17, 2007 Office Action, issued in connection with U.S. Appl. No. 10/477,469.
Oct. 17, 2007 Response to Office Action, filed in connection with U.S. Appl. No. 10/477,469.
Jan. 14, 2008 Response to Office Action, filed in connection with U.S. Appl. No. 10/477,469.
Apr. 17, 2008 Office Action, issued in connection with U.S. Appl. No. 10/477,469.
Aug. 15, 2008 Request for Continued Examination and Amendment, filed in connection with U.S. Appl. No. 10/477,469.
Nov. 26, 2008 Office Action, issued in connection with U.S. Appl. No. 10/477,469.
Mar. 26, 2009 Response to Office Action, filed in connection with U.S. Appl. No. 10/477,469.
Jun. 12, 2009 Office Action, issued in connection with U.S. Appl. No. 10/477,469.
Nov. 11, 2009 Request for Continued Examination and Amendment, filed in connection with U.S. U.S. Appl. No. 10/477,469.
Feb. 1, 2010 Office Action, issued in connection with U.S. Appl. No. 10/477,469.
Aug. 2, 2010 Response to Office Action, filed in connection with U.S. Appl. No. 10/477,469.
Oct. 15, 2010 Office Action, issued in connection with U.S. Appl. No. 10/477,469.
Jun. 17, 2011 Request for Continued Examination and Amendment, filed in connection with U.S. Appl. No. 10/477,469.
Aug. 12, 2011 Preliminary Amendment and Summary of Examiner Interview, filed in connection with U.S. Appl. No. 10/477,469.
Jun. 18, 2012 Office Action and Examiner Interview Summary, issued in connection with U.S. Appl. No. 10/477,469.
Jun. 18, 2012 Response to Office Action and Examiner Interview Summary, filed in connection with U.S. Appl. No. 10/477,469.
Jun. 25, 2012 Examiner Interview Summary and Notice of Allowance, issued in connection with U.S. Appl. No. 10/477,469.
May 3, 2012 Office Action issued in connection with Chinese Patent Application No. 201110126434.2, including English Language Translation.
Nov. 19, 2012 Response filed in connection with Chinese Patent Application No. 201110126434.2, including English-Language claims.
Mar. 13, 2013 Office Action issued in connection with Chinese Patent Application No. 201110126434.2, including English Language Translation.
Apr. 8, 2013 Office Action, issued in connection with Chinese Patent Application Publication No. 201210084310.7, including English Language Translation.

\* cited by examiner

```
   1  ATGCAAACGA GAAGAGATGC ACTTAAGTCT GCGGCCGCAA TAACTCTGCT
  51  CGGCGGCTTG GCTGGGTGTG CAAGCATGGC CCGACCAATC GGTACAGGCG
 101  ATCTGATTAA TACTGTTCGC GGCCCCATTC CAGTTTCGGA AGCGGGCTTC
 151  ACACTGACCC ATGAGCATAT CTGCGGCAGT TCGGCGGGAT TCCTACGTGC
 201  GTGGCCGGAG TTTTTCGGTA GCCGCAAAGC TCTAGCGGAA AAGGCTGTGA
 251  GAGGATTACG CCATGCCAGA TCGGCTGGCG TGCAAACCAT CGTCGATGTG
 301  TCGACTTTCG ATATCGGTCG TGACGTCCGT TTATTGGCCG AAGTTTCGCG
 351  GGCCGCCGAC GTGCATATCG TGGCGGCGAC TGGCTTATGG TTCGACCCGC
 401  CACTTTCAAT GCGAATGCGC AGCGTCGAAG AACTGACCCA GTTCTTCCTG
 451  CGTGAAATCC AACATGGCAT CGAAGACACC GGTATTAGGG CGGGCATTAT
 501  CAAGGTCGCG ACCACAGGGA AGGCGACCCC CTTTCAAGAG TTGGTGTTAA
 551  AGGCAGCCGC GCGGGCCAGC TTGGCCACCG GTGTTCCGGT AACCACTCAC
 601  ACGTCAGCAA GTCAGCGCGA TGGCGAGCAG CAGGCAGCCA TATTTGAATC
 651  CGAAGGTTTG AGCCCCTCAC GGGTTTGTAT CGGTCACAGC GATGATACTG
 701  ACGATTTGAG CTACCTAACC GGCCTCGCTG CGCGCGGATA CCTCGTCGGT
 751  TTAGATCGCA TGCCGTACAG TGCGATTGGT CTAGAAGGCA ATGCGAGTGC
 801  ATTAGCGCTC TTTGGTACTC GGTCGTGGCA AACAAGGGCT CTCTTGATCA
 851  AGGCGCTCAT CGACCGAGGC TACAAGGATC GAATCCTCGT CTCCCATGAC
 901  TGGCTGTTCG GGTTTTCGAG CTATGTCACG AACATCATGG ACGTAATGGA
 951  TCGCATAAAC CCAGATGGAA TGGCCTTCGT CCCTCTGAGA GTGATCCCAT
1001  TCCTACGAGA GAAGGGCGTC CGCCGGAAA  CGCTAGCAGG CGTAACCGTG
1051  GCCAATCCCG CGCGGTTCTT GTCACCGACC GTGCGGGCCG TCGTGACACG
1101  ATCTGAAACT TCCCGCCCTG CCGCGCCTAT TCCCCGTCAA GATACCGAAC
1151  GATGA
```

Figure 2

```
  1  MQTRRDALKS  AAAITLLGGL  AGCASMARPI  GTGDLINTVR  GPIPVSEAGF
 51  TLTHEHICGS  SAGFLRAWPE  FFGSRKALAE  KAVRGLRHAR  SAGVQTIVDV
101  STFDIGRDVR  LLAEVSRAAD  VHIVAATGLW  FDPPLSMRMR  SVEELTQFFL
151  REIQHGIEDT  GIRAGIIKVA  TTGKATPFQE  LVLKAAARAS  LATGVPVTTH
201  TSASQRDGEQ  QAAIFESEGL  SPSRVCIGHS  DDTDDLSYLT  GLAARGYLVG
251  LDRMPYSAIG  LEGNASALAL  FGTRSWQTRA  LLIKALIDRG  YKDRILVSHD
301  WLFGFSSYVT  NIMDVMDRIN  PDGMAFVPLR  VIPFLREKGV  PPETLAGVTV
351  ANPARFLSPT  VRAVVTRSET  SRPAAPIPRQ  DTER
```

Figure 3

```
OPD      1  MQTRRVVLKSAAAAGTLLGGLAGCASVAGSIGTGDRINTVRGPITISEAG   50
            |||||  ||||||  ||||||||||||:|  |||||  ||||||||.:||||
OpdA     1  MQTRRDALKSAAAI.TLLGGLAGCASMARPIGTGDLINTVRGPIPVSEAG   49

OPD     51  FTLTHEHICGSSAGFLRAWPEFFGSRKALAEKAVRGLRRARAAGVRTIVD  100
            ||||||||||||||||||||||||||||||||||||||:||.|||.||||
OpdA    50  FTLTHEHICGSSAGFLRAWPEFFGSRKALAEKAVRGLRHARSAGVQTIVD   99

OPD    101  VSTFDIGRDVSLLAEVSRAADVHIVAATGLWFDPPLSMRLRSVEELTQFF  150
            ||||||||.|||||||||||||||||||||||||||||:||||||||||
OpdA    99  VSTFDIGRDVRLLAEVSRAADVHIVAATGLWFDPPLSMRMRSVEELTQFF  149

OPD    151  LREIQYGIEDTGIRAGIIKVATTGKATPFQELVLKAAARASLATGVPVTT  200
            |||||.||||||||||||||||||||||||||||||||||||||||||||
OpdA   150  LREIQHGIEDTGIRAGIIKVATTGKATPFQELVLKAAARASLATGVPVTT  199

OPD    201  HTAASQRDGEQQAAIFESEGLSPSRVCIGHSDDTDDLSYLTALAARGYLI  250
            ||.|||||||||||||||||||||||||||||||||||||||:|||||||:
OpdA   200  HTSASQRDGEQQAAIFESEGLSPSRVCIGHSDDTDDLSYLTGLAARGYLV  249

OPD    251  GLDHIPHSAIGLEDNASASALLGIRSWQTRALLIKALIDQGYMKQILVSN  300
            |||::|.||||||:|||| ||:|.|||||||||||||||.||...||||:
OpdA   250  GLDRMPYSAIGLEGNASALALFGTRSWQTRALLIKALIDRGYKDRILVSH  299

OPD    301  DWLFGFSSYVTNIMDVMDRVNPDGMAFIPLRVIPFLREKGVPQETLAGIT  350
            ||||||||||||||||||||:|||||||:||||||||||||.|||||:|
OpdA   300  DWLFGFSSYVTNIMDVMDRINPDGMAFVPLRVIPFLREKGVPPETLAGVT  349

OPD    351  VTNPARFLSPTLRAS  365
            |.|||||||||:||
OpdA   350  VANPARFLSPTVRAVVTRSETSRPAAPIPRQDTER  384
```

Figure 4

PHOSPHOTRIESTERASE FROM AGROBACTERIUM RADIOBACTER P230

This application is a divisional of U.S. Ser. No. 10/477,469, now U.S. Pat. No. 8,293,244, issued Oct. 23, 2012, a §371 national stage of PCT International Application No. PCT/AU2002/00594, filed May 15, 2002, claiming priority of Australian Patent Application No. PR 5023, filed May 15, 2001, the contents of each of which are hereby incorporated by reference.

FIELD OF THE INVENTION

This invention relates to enzymes capable of hydrolyzing organophosphate (OP) molecules. In particular, the invention relates to a phosphotriesterase enzyme identified from an *Agrobacterium radiobacter* strain isolated from soil that hydrolyses OP pesticides, and the gene encoding that enzyme. The invention also relates to mutants of the identified phosphotriesterase enzyme which have altered substrate specificity.

BACKGROUND OF THE INVENTION

Residues of organophosphate insecticides are undesirable contaminants of the environment and a range of commodities. Areas of particular sensitivity include contamination of soil, irrigation tailwater that is re-cycled, used by irrigators downstream or simply allowed to run off-farm, and residues above permissible levels in agricultural and horticultural exports. Poisoning with organophosphates presents a problem for agricultural workers that are exposed to these chemicals, as well as military personnel exposed to organophosphates used in chemical warfare. Furthermore, the stockpiling of organophosphorus nerve agents has resulted in the need to detoxify these stocks. Bioremediation strategies are therefore required for eliminating or reducing these organophosphate residues and/or stockpiles.

One proposed strategy involves the use of enzymes capable of immobilising or degrading the organophosphate residues. Such enzymes may be employed, for example, in bioreactors through which contaminated water could be passed, or in washing solutions after post-harvest disinfestation of fruit, vegetables or animal products to reduce residue levels and withholding times. Suitable enzymes for degrading organophosphate residues include OP hydrolases from bacteria (Mulbry, 1992; Mulbry and Kearney, 1991; Cheng et al., 1999; U.S. Pat. No. 5,484,728; U.S. Pat. No. 5,589,386), vertebrates (Wang et al., 1993; 1998; Gan at al, 1991; Broomfield et al., 1999) and OP resistant insects (WO 95/19440 and WO 97/19176). It is desirable that the OP hydrolases degrade the organophosphate residues at a rapid rate.

The most thoroughly studied OP degrading enzyme is bacterial organophosphate dihydrolase (OPD), which is encoded by identical genes on dissimilar plasmids in both *Flavobacterium* sp. ATCC 27551 and *Brevundimonas diminuta* MG (Harper of al., 1988; Mulbry and Karns, 1989). OPD is a homodimeric protein that is capable of hydrolysing a wide range of phosphate triesters (both oxon and thion OPs) (Dumas et al., 1989a, b). Its reaction mechanism directly or indirectly involves metal ions, preferably $Zn^{++}$. OPD has no detectable activity with phosphate monoesters or diesters (Dumas et al., 1989a, b; 1990).

OPD homologues (phosphotriesterase homology proteins, or PHPs) have been identified in the genomes of *Escherichia coli* (ePHP), *Mycobacterium tuberculosis* (mtPHP) and *Mycoplasma pneumoniae* (mpPHP), although only ePHP has been tested for phosphotriesterase activity (Scanlan and Reid, 1995; Buchbinder et al., 1998). No activity was detected in ePHP crude lysates with any of the substrates tested, such as p-nitrophenyl acetate, bis(p-nitrophenyl) phosphate, paraoxon and p-nitrophenyl phosphate.

OPD homologues have also been identified in vertebrates (Davies et al., 1997), although their function in these organisms is unknown. OPD, ePHP, mtPHP and mammalian PHPs are 27-30% identical at the amino acid level, while mpPHP is less similar. Amino acid residues involved in $Zn^{++}$ binding are conserved across the six members of the phosphotriesterase family identified to date (Buchbinder et al., 1998).

Three other distinct OP hydrolysing enzymes have been isolated from bacteria with a history of exposure to OPs (Mulbry and Karns, 1989; Mulbry, 1992; Cheng et al., 1999). The two for which sequence data are available are unrelated to each other and to OPD. One, a prolidase from *Alteromonas* sp., normally functions in hydrolysis of X-Pro dipeptides. Its activity for insecticidal OPs is reported as modest, although it has not been reported in terms of $k_{cat}/K_m$ specificity constants (Cheng et al., 1999). The other, an aryldialkylphosphatase (ADPase) from *Nocardia* sp. strain B-1, has a turnover number for ethyl parathion that is 4500-fold lower than that reported for OPD (Mulbry and Karns, 1989; Mulbry, 1992).

Paraoxonase, or PON1, is a distinct OP hydrolysing enzyme found in mammals. Like OPD it is a metalloenzyme, preferring $Ca^{++}$ in this case, which is associated with low density lipoproteins in plasma and normally involved in metabolism of oxidised lipid compounds (Gan et al., 1991; Sorenson et al., 1995). It has high activity for paraoxon, with a specificity constant of around $10^6$ $M^{-1}sec^{-1}$ (Doom et al., 1999; Hong and Raushel, 1999).

There is also evidence for other, so-called diisopropyl fluorophosphatase (DFPase) enzymes in a wide range of vertebrates, invertebrates and microorganisms (Wang et al., 1998; Hoskin et al., 1999; Billecke et al., 1999). These enzymes are notably diverse in many of their biochemical properties but are all characterised by their hydrolytic activity against OP chemical warfare agents. Limited sequence data suggest that they are unrelated to all the other OP hydrolytic enzymes described above.

OP resistant blowflies and houseflies have been the source of esterase enzymes with activity against oxon OPs like chlorfenvinfos (CVP) and carboxylester OPs like malathion (Newcomb et al., 1997; Campbell et al. 1998; Claudianos et al. 1999; WO 95/19440; WO 97/19176). A Gly to Asp substitution at residue 137 in blowfly esterase E3 (and its housefly ortholog, ALI) resulted in the acquisition of activity for CVP, while a Trp to Leu/Ser mutation at residue 251 in the same enzyme resulted in activity against malathion. However, the specificity constants of these enzymes for their OP substrates are orders of magnitude less than those of OPD for paraoxon.

There is a need for further OP degrading enzymes which can be used in bioremediation strategies.

SUMMARY OF THE INVENTION

The present inventors have developed a rapid and sensitive fluorimetric assay for coumaphos (a thion OP insecticide) hydrolysis and used it to isolate a bacterium from contaminated soil that is capable of using OPs as the sole phosphorus source. 16S rDNA sequencing identified the bacterium (isolate P230) as a strain of *Agrobacterium radiobacter*. The present inventors have also isolated and characterized the enzyme responsible for this coumaphos hydrolytic activity and provide methods for the use of this enzyme in bioremediation strategies.

In one aspect, the present invention provides a substantially purified polypeptide, the polypeptide being selected from:
(i) a polypeptide comprising a sequence provided in SEQ ID NO:1;
(ii) a polypeptide comprising a sequence provided in SEQ ID NO:2;
(iii) a polypeptide comprising a sequence provided in SEQ ID NO:3;
(iv) a polypeptide comprising a sequence provided in SEQ ID NO:4; or
(v) a polypeptide comprising a sequence which is greater than 90% identical to any one of (i) to (iv),
wherein the polypeptide is capable of hydrolysing an organophosphate molecule.

Preferred organophosphate molecules include, but are not limited to, coumaphos, coroxon, paraoxon, parathion, parathion-methyl, phosmet, fenthion, diazinon, chlorpyrifos, dMUP, DFP, dimethoate, malathion, and malaoxon. More preferably, the organophosphate is phosmet or fenthion.

In a preferred embodiment, the polypeptide can be purified from an *Agrobacterium* sp.

In a further preferred embodiment, the polypeptide is at least 95% identical to any one of (i) to (iv), more preferably at least 97% identical, and even more preferably at least 99% identical to any one of (i) to (iv).

In another aspect, the present invention provides a substantially purified polypeptide, the polypeptide being selected from:
(i) a polypeptide comprising the sequence provided in SEQ ID NO:1;
(ii) a polypeptide comprising the sequence provided in SEQ ID NO:2; or
(iii) a polypeptide which is greater than 90% identical to (i) or (ii).

In another aspect, a fusion polypeptide is provided which comprises a polypeptide according to the present invention fused to at least one other polypeptide sequence.

Preferably, the at least one other polypeptide is selected from the group consisting of: a polypeptide that enhances the stability of the polypeptide of the invention, and a polypeptide that assists in the purification of the fusion polypeptide.

Preferably, the at least one other polypeptide is the maltose-binding protein.

In another aspect, the present invention provides an isolated polynucleotide, the polynucleotide comprising a sequence selected from:
(i) a sequence of nucleotides shown in SEQ ID NO:5;
(ii) a sequence of nucleotides shown in SEQ ID NO:6;
(iii) a sequence of nucleotides shown in SEQ ID NO:7;
(iv) a sequence of nucleotides shown in SEQ ID NO:8;
(v) a sequence encoding a polypeptide according to the present invention; or
(vi) a sequence which is at least 90% identical to any one of (i) to (v),
wherein the polynucleotide encodes a polypeptide capable of hydrolysing an organophosphate molecule.

Preferably, the polynucleotide is at least 95% identical, more preferably at least 97% identical, and even more preferably at least 99% identical to any one of (i) to (v).

In a further aspect, a vector is provided which comprises a polynucleotide according to the invention.

Preferably, the vector is suitable for the replication and/or expression of a polynucleotide. The vectors may be, for example, a plasmid, virus or phage vector provided with an origin of replication, and preferably a promotor for the expression of the polynucleotide and optionally a regulator of the promotor. The vector may contain one or more selectable markers, for example an ampicillin resistance gene in the case of a bacterial plasmid or a neomycin resistance gene for a mammalian expression vector. The vector may be used in vitro, for example for the production of RNA or used to transfect or transform a host cell.

In another aspect, a host cell is provided which comprises a vector according to the invention.

In a further aspect, the present invention provides a process for preparing a polypeptide of the invention, the process comprising cultivating a host cell of the invention under conditions which allow production of the polypeptide, and recovering the polypeptide. Such cells can be used for the production of commercially useful quantities of the encoded polypeptide.

In another aspect, the present invention provides a composition for hydrolysing an organophosphate molecule, the composition comprising a polypeptide according to the invention, and one or more acceptable carriers.

In another aspect, the present invention provides a composition for hydrolysing an organophosphate molecule, the composition comprising a host cell of the invention, and one or more acceptable carriers.

It will be appreciated that the present invention can be used to hydrolyse organophosphates in a sample. For instance, after a crop has been sprayed with an organophosphate pesticide, the organophosphate residue can be hydrolysed from seeds, fruits and vegetables before human consumption. Similarly, organophosphate contaminated soil or water can be treated with a polypeptide of the invention.

Accordingly, in a further aspect the present invention provides a method for hydrolysing an organophosphate molecule in a sample, the method comprising exposing the sample to a polypeptide according to the invention.

Preferably, the polypeptide is provided as a composition of the invention.

Further, it is preferred that the method further comprises exposing the sample to a divalent cation. Preferably, the divalent cation is zinc.

Preferably, the sample is selected from the group consisting of; soil, water, biological material, or a combination thereof. Preferred biological samples include matter derived from plants such as seeds, vegetables or fruits, as well as matter derived from animals such as meat.

Preferred organophosphate molecules include, but are not limited to, coumaphos, coroxon, paraoxon, parathion, parathion-methyl, phosmet, fenthion, diazinon, chlorpyrifos, dMUP, DFP, dimethoate, malathion, and malaoxon. More preferably, the organophosphate is phosmet or fenthion.

The sample can be exposed to the polypeptide via any available avenue. This includes providing the polypeptide directly to the sample, with or without carriers or excipients etc. The polypeptide can also be provided in the form of a host cell, typically a microorganism such as a bacterium or a fungus, which expresses a polynucleotide encoding the polypeptide of the invention. Usually, the polypeptide will be provided as a composition of the invention.

Organophosphate molecules in a sample can also be hydrolysed by exposing the sample to a transgenic plant which produces a polypeptide of the present invention.

Thus, in a further aspect a transgenic plant is provided which produces a polypeptide according to the invention.

In a further aspect, the present invention provides a method for hydrolysing an organophosphate molecule in a sample, the method comprising exposing the sample to a transgenic plant according to the invention.

Preferably, the sample is soil.

Further, it is preferred that the polypeptide is at least produced in the roots of the transgenic plant.

In yet another aspect, the present invention provides an isolated strain of *Agrobacterium radiobacter* deposited under NM01/21112 on 20 Apr. 2001 at Australian Government Analytical Laboratories.

In another aspect, the present invention provides a composition for hydrolysing an organophosphate molecule, the composition comprising the *Agrobacterium radiobacter* strain of the invention, and one or more acceptable carriers.

In yet another aspect, the present invention provides a method for hydrolysing an organophosphate molecule in a sample, the method comprising exposing the sample to an *Agrobacterium radiobacter* strain according to the invention.

The disclosure of the present invention can readily be used to isolate other bacterial species/strains which hydrolyse organophosphates. For example, other bacterial species/strains may be isolated using a fluormetric screening method as disclosed herein. Alternatively, probes and/or primers can be designed based on the polynucleotides of the present invention to identify bacteria which produce naturally occurring variants of the polypeptides of the present invention.

Accordingly, in a further aspect the present invention provides an isolated bacterium which produces a polypeptide according to the invention.

Preferably, the bacterium is an *Agrobacterium* sp. More preferably, the bacterium is a strain of *Agrobacterium radiobacter*.

In a further aspect, the present invention provides the use of an isolated naturally occurring bacterium which produces a polypeptide according to the invention for hydrolysing an organophosphate in a sample.

In a further aspect, the present invention provides a polymeric sponge or foam for hydrolysing an organophosphate molecule, the foam or sponge comprising a polypeptide according to the invention immobilized on a polymeric porous support.

Preferably, the porous support comprises polyurethane.

In a preferred embodiment, the sponge or foam further comprises carbon embedded or integrated on or in the porous support.

In a further aspect, the present invention provides a method for hydrolysing an organophosphate molecule in a sample, the method comprising exposing the sample to a sponge or foam according to the invention.

In another aspect, the present invention provides a biosensor for detecting the presence of an organophosphate, the biosensor comprising a polypeptide of the invention, and a means for detecting hydrolysis of an organophosphate molecule by the polypeptide.

In yet another aspect, the present invention provides a method for screening for agents which hydrolyse an organophosphate molecule, the method comprising
(i) exposing the organophosphate to a candidate agent, and
(ii) measuring a fluorescent signal produced from step (i), wherein the fluorescent signal is indicative of hydrolysis of the organophosphate.

Preferably, the organophosphate is coumaphos or coroxon.

Further, it is preferred that the agent is a polypeptide or a micro-organism.

The polypeptide of the present invention can be mutated, and the resulting mutants screened for altered activity such as changes in substrate specificity.

Thus, in a further aspect, the present invention provides a method of producing a polypeptide with enhanced ability to hydrolyse an organophosphate or altered substrate specificity for an organophosphate, the method comprising
i) mutating one or more amino acids of a first polypeptide according to the present invention,
ii) determining the ability of the mutant to hydrolyse an organophosphate, and
iii) selecting a mutant with enhanced ability to hydrolyse the organophosphate or altered substrate specificity for the organophosphate, when compared to the first polypeptide.

As outlined in the Example section, this method has been successfully applied to produce the polypeptides provided as SEQ ID NO:2 and SEQ ID NO:3.

Preferably, the first polypeptide is selected from any one if SEQ ID NO's: 1 to 4.

In a further aspect, the present invention provides a polypeptide produced according to the above method.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention will hereinafter be described by way of the following non-limiting Figures and Examples.

BRIEF DESCRIPTION OF THE DRAWINGS

FIG. 2: The DNA sequence of opdA (SEQ ID NO:5). The region encoding the signal peptide domain is given in bold, with the remaining sequence being referred to herein as SEQ ID NO:6.

FIG. 3: Amino acid sequence of OpdA (SEQ ID NO:1). The signal peptide is given in bold.

FIG. 4: Amino acid sequence alignment of OPD (SEQ ID NO:17) and OpdA. The secretion signals are given in bold.

KEY TO THE SEQUENCE LISTING

Figure 1:
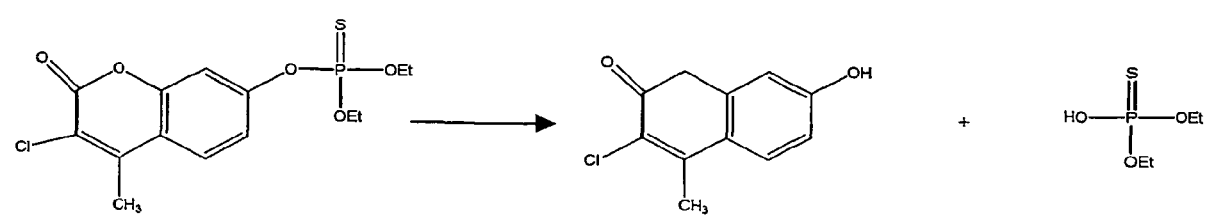
FIG. 1: Structure of coumaphos and its hydrolysis products.

SEQ ID NO: 1—Polypeptide sequence of OpdA.
SEQ ID NO: 2—Polypeptide sequence of OpdA minus the signal sequence.
SEQ ID NO: 3—Polypeptide sequence of OpdA1.
SEQ ID NO: 4—Polypeptide sequence of OpdA2.
SEQ ID NO: 5—Polynucleotide sequence encoding OpdA.
SEQ ID NO: 6—Polynucleotide sequence encoding OpdA minus the signal sequence.
SEQ ID NO: 7—Polynucleotide sequence encoding OpdA1.
SEQ ID NO: 8—Polynucleotide sequence encoding OpdA2.
SEQ ID NO's: 9 to 16—PCR primers.
SEQ ID NO: 17—Polypeptide sequence of OPD from *Flavobacterium* sp.

DETAILED DESCRIPTION OF THE INVENTION

General Techniques

Unless otherwise indicated, the recombinant DNA techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (Editors), Current Protocols in Molecular Biology, Greene Pub. Associates and Wiley-Interscience (1988, including all updates until present).

Organophosphates

Organophosphates are synthetic organophosphorus esters and related compounds such as phosphoroamidates. They have the general formula (RR'X)P=O or (RR'X)P=S, where R and R' are short-chain groups. For insecticidal organophosphates X is a good leaving group, which is a requirement for the irreversible inhibition of acetylcholinesterase.

The polypeptides of the present invention hydrolyse the phosphoester bonds of organophosphates. These organophosphates can be, but are not limited to, oxon and thion OPs. The organophosphate can have aromatic or aliphatic leaving groups (X).

Although well known for their use as pesticides, organophosphates have also been used as nerve gases against mammals. Accordingly, it is envisaged that the polypeptides of the present invention will also be useful for hydrolysis of organophosphates which are not pesticides.

Polypeptides

By "substantially purified polypeptide" we mean a polypeptide that has generally been separated from the lipids, nucleic acids, other polypeptides, and other contaminating molecules with which it is associated in its native state. Preferably, the substantially purified polypeptide is at least 60% free, more preferably at least 75% free, and most preferably at least 90% free from other components with which they are naturally associated.

The % identity of a polypeptide is determined by FASTA (Pearson and Lipman, 1988) analysis (GCG program) using the default settings and a query sequence of at least 50 amino acids in length, and whereby the FASTA analysis aligns the two sequences over a region of at least 50 amino acids. More preferably, the FASTA analysis aligns the two sequences over a region of at least 100 amino acids. More preferably, the FASTA analysis aligns the two sequences over a region of at least 250 amino acids. Even more preferably, the FASTA analysis aligns the two sequences over a region of at least 350 amino acids.

Amino acid sequence mutants of the polypeptides of the present invention can be prepared by introducing appropriate nucleotide changes into a nucleic acid sequence, or by in vitro synthesis of the desired polypeptide. Such mutants include, for example, deletions, insertions or substitutions of residues within the amino acid sequence. A combination of deletion, insertion and substitution can be made to arrive at the final construct, provided that the final protein product possesses the desired characteristics. Examples of mutants of the present invention are provided in Example 8.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 30 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

Since the sequence of SEQ ID NO:1 is 90% identical to that of the *Flavobacterium* OPD enzyme it is possible that SEQ ID NO:1 could be used to design mutants of the *Flavobacterium* OPD enzyme which have the desired activity but are less than 90% identical. More specifically, those amino acids important for hydrolysing an organophosphate molecule could be changed to match the polypeptides of the present invention and other amino acids not affecting this activity could also be changed to ensure the identity levels do not exceed 90%. Examples of such OPD mutants include the amino acid changes L272F and/or H257Y. Such mutants are also included in the present invention.

TABLE 1

Exemplary substitutions

| Original Residue | Exemplary Substitutions |
|---|---|
| Ala (A) | val; leu; ile; gly |
| Arg (R) | lys |
| Asn (N) | gln; his; |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe; |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Furthermore, if desired, unnatural amino acids or chemical amino acid analogues can be introduced as a substitution or addition into the polypeptide of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Polypeptides of the present invention can be produced in a variety of ways, including production and recovery of natural proteins, production and recovery of recombinant proteins, and chemical synthesis of the proteins. In one embodiment, an isolated polypeptide of the present invention is produced by culturing a cell capable of expressing the polypeptide under conditions effective to produce the polypeptide, and recovering the polypeptide. Effective culture conditions include, but are not limited to, effective media, bioreactor, temperature, pH and oxygen conditions that permit protein production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Polynucleotides

By "isolated polynucleotide" we mean a polynucleotide which have generally been separated from the polynucleotide sequences with which it is associated or linked in its native state. Preferably, the isolated polynucleotide is at least 60% free, more preferably at least 75% free, and most preferably at least 90% free from other components with which they are naturally associated. Furthermore, the term "polynucleotide" is used interchangeably herein with the term "nucleic acid molecule".

Polynucleotides of the present invention may possess one or more mutations when compared to SEQ ID NO's: 5 to 8. These mutations can be deletions, insertions, or substitutions of nucleotide residues. Mutants can be either naturally occurring (that is to say, isolated from a natural source) or synthetic (for example, by performing site-directed mutagenesis on the nucleic acid). It is thus apparent that polynucleotides of the invention can be either naturally occurring or recombinant.

The % identity of a polynucleotide is determined by FASTA (Pearson and Lipman, 1988) analysis (GCG program) using the default settings and a query sequence of at least 150 nucleotides in length, and whereby the FASTA analysis aligns the two sequences over a region of at least 150 nucleotides. More preferably, the FASTA analysis aligns the two sequences over a region of at least 300 nucleotides. Even more preferably, the FASTA analysis aligns the two sequences over a region of at least 1050 nucleotides.

Oligonucleotides of the present invention can be RNA, DNA, or derivatives of either. The minimum size of such oligonucleotides is the size required for the formation of a stable hybrid between an oligonucleotide and a complementary sequence on a nucleic acid molecule of the present invention. The present invention includes oligonucleotides that can be used as, for example, probes to identify nucleic acid molecules or primers to produce nucleic acid molecules.

Oligonucleotides and/or polynucleotides of the present invention may selectively hybridise to the sequences set out in SEQ ID NO's: 5 to 8 under high stringency. As used herein, stringent conditions are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Vectors

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

One type of recombinant vector comprises a nucleic acid molecule of the present invention operatively linked to an expression vector. The phrase operatively linked refers to the insertion of a nucleic acid molecule into an expression vector in a manner such that the molecule is able to be expressed when transformed into a host cell. As used herein, an expression vector is a DNA or RNA vector that is capable of transforming a host cell and effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, other animal, and plant cells. Preferred expression vectors of the present invention can direct gene expression in bacterial, yeast, plant and mammalian cells.

Expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the host cells of the present invention. A variety of such transcription control sequences are known to those skilled in the art. Preferred transcription control sequences include those which function in bacterial, yeast, plant and mammalian cells, such as, but not limited to, tac, lac, trp, trc, oxy-pro, omp/lpp, rrnB, bacteriophage lambda, bacteriophage T7, T7lac, bacteriophage T3, bacteriophage SP6, bacteriophage SP01, metallothionein, alpha-mating factor, *Pichia* alcohol oxidase, aiphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers.

Recombinant molecules of the present invention may also (a) contain secretory signals (i.e., signal segment nucleic acid sequences) to enable an expressed polypeptide of the present invention to be secreted from the cell that produces the polypeptide and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal sequences. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention.

Host Cells

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells can be either untransformed cells or cells that are already transformed with at least one nucleic acid molecule (e.g., nucleic acid molecules encoding one or more proteins of the present invention). Host cells of the present invention either can be endogenously (i.e., naturally) capable of producing proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite, arthropod, animal and plant cells. Preferred host cells include bacterial, mycobacterial, yeast, plant and mammalian cells. More preferred host cells include *Agrobacterium, Salmonella, Escherichia, Bacillus, Listeria, Saccharomyces, Spodoptera, Mycobacteria, Trichoplusia*, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *E. coli*, including *E. coli* K-12 derivatives; *Salmonella typhi*; *Salmonella typhimurium*, including attenuated strains; *Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK cells and/or HeLa cells.

Recombinant DNA technologies can be used to improve expression of transformed polynucleotide molecules by manipulating, for example, the number of copies of the polynucleotide molecules within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts. The activity of an expressed recombinant protein of the present invention may be improved by fragmenting, modifying, or derivatizing polynucleotide molecules encoding such a protein.

Transgenic Plants

As generally described in WO 99/53037, the levels of organophosphates in a sample can be reduced by exposing the sample to a transgenic plant expressing a suitable enzyme. Typically, the sample is soil. Accordingly, the polynucleotide of the present invention can be expressed in a transgenic plant, particularly the roots of the plant, for hydrolysing organophosphate molecules in the sample.

The term "plant" refers to whole plants, plant organs (e.g. leaves, stems roots, etc), seeds, plant cells and the like. Plants contemplated for use in the practice of the present invention include both monocotyledons and dicotyledons. Exemplary dicotyledons include cotton, corn, tomato, tobacco, potato, bean, soybean, and the like.

Transgenic plants, as defined in the context of the present invention include plants (as well as parts and cells of said plants) and their progeny which have been genetically modified using recombinant DNA techniques to cause or enhance production of at least one protein of the present invention in the desired plant or plant organ.

The polypeptide of the present invention may be expressed constitutively in the transgenic plants during all stages of development. Depending on the use of the plant or plant organs, the proteins may be expressed in a stage-specific manner. Furthermore, depending on the use, the proteins may be expressed tissue-specifically.

The choice of the plant species is determined by the intended use of the plant or parts thereof and the amenability of the plant species to transformation.

Regulatory sequences which are known or are found to cause expression of a gene encoding a protein of interest in plants may be used in the present invention. The choice of the regulatory sequences used depends on the target plant and/or target organ of interest. Such regulatory sequences may be obtained from plants or plant viruses, or may be chemically synthesized. Such regulatory sequences are well known to those skilled in the art.

Other regulatory sequences such as terminator sequences and polyadenylation signals include any such sequence functioning as such in plants, the choice of which would be obvious to the skilled addressee. An example of such sequences is the 3' flanking region of the nopaline synthase (nos) gene of *Agrobacterium tumefaciens*.

Several techniques are available for the introduction of the expression construct containing a DNA sequence encoding a protein of interest into the target plants. Such techniques include but are not limited to transformation of protoplasts using the calcium/polyethylene glycol method, electroporation and microinjection or (coated) particle bombardment. In addition to these so-called direct DNA transformation methods, transformation systems involving vectors are widely available, such as viral and bacterial vectors (e.g. from the genus *Agrobacterium*). After selection and/or screening, the protoplasts, cells or plant parts that have been transformed can be regenerated into whole plants, using methods known in the art. The choice of the transformation and/or regeneration techniques is not critical for this invention.

Compositions

Compositions of the present invention include excipients, also referred to herein as "acceptable carriers". An excipient can be any material that the animal, plant, plant or animal material, or environment (including soil and water samples) to be treated can tolerate. Examples of such excipients include water, saline, Ringers solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal or o-cresol, formalin and benzyl alcohol. Excipients can also be used to increase the half-life of a composition, for example, but are not limited to, polymeric controlled release vehicles, biodegradable implants, liposomes, bacteria, viruses, other cells, oils, esters, and glycols.

Furthermore, the polypeptide of the present invention can be provided in a composition which enhances the rate and/or degree of organophosphate hydrolysis, or increases the stability of the polypeptide. For example, the polypeptide can be immobilized on a polyurethane matrix (Gordon et al., 1999), or encapsulated in appropriate liposomes (Petrikovics et al. 2000a and b). The polypeptide can also be incorporated into a composition comprising a foam such as those used routinely in fire-fighting (LeJeune et al., 1998). As would be appreciated by the skilled addressee, the polypeptide of the present invention could readily be used in a sponge or foam as disclosed in WO 00/64539, the contents of which are incorporated herein in their entirety.

One embodiment of the present invention is a controlled release formulation that is capable of slowly releasing a composition of the present invention into an animal, plant, animal or plant material, or the environment (including soil and water samples). As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Preferred controlled release formulations are biodegradable (i.e., bioerodible).

A preferred controlled release formulation of the present invention is capable of releasing a composition of the present invention into soil or water which is in an area sprayed with an organophosphate pesticide. The formulation is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

The concentration of the polypeptide, vector, or host cell of the present invention that will be required to produce effective compositions for hydrolysing an organophosphate will depend on the nature of the sample to be decontaminated, the concentration of the organophosphate in the sample, and the formulation of the composition. The effective concentration of the polypeptide, vector, or host cell within the composition can readily be determined experimentally, as will be understood by the skilled artisan.

Biosensors

Biosensors are analytical devices typically consisting of a biologically active material such as an enzyme and a transducer that converts a biochemical reaction into a quantifiable electronic signal that can be processed, transmitted, and measured. A general review of biosensors which have been used for the detection of orangophosphorus compounds is provided by Rekha et al. (2000), the entire contents of which are incorporated by reference. The polypeptide of the present invention can be adapted for use in such biosensors.

EXAMPLES

Example 1

Enriching Soil Samples for Microorganisms with Coumaphos Hydrolytic Activity

Fluorimetric Assay for Coumaphos Hydrolysis

Phosphotriesterase enzymes catalyse the cleavage of a phosphoester bond in organophosphate (OP) molecules to yield a phosphodiester and an alcohol: In the case of coumaphos (3-chloro-4-methyl-7-coumarinyl diethyl phosphorothioate), phosphotriesterase hydrolysis yields diethylthiophosphate and the fluorescent alcohol, chlorferon (3-chloro-7-hydroxy-4-methyl coumarin; FIG. 1). Coumaphos hydrolysis can therefore be measured fluorimetrically by the production of chlorferon, as measured by excitation at a wavelength of 355 nm and an emission intensity of 460 nm. Chlorferon fluorescence was linear over the range 0.01 µM to 2.5 µM.

All fluorescence measurements were performed in a POLARstar fluorimeter (BMG Technologies Pty Ltd, Australia) using 96-well white microtitre plates (FluoroNunc plates with PolySorp surface, Nalge Nunc International) and final reaction volumes of 100 µl. Stock solutions of coumaphos and chlorferon (0.4 mM) were prepared in 20% methanol. Crude assays of whole cells were performed in 100 µM coumaphos, 0.5% Triton X-100 and 50 mM Tris-HCl, pH8.0. Coumaphos hydrolytic assays of cell lysates were performed without the Triton X-100.

The fluorescence of bacterial colonies and stained polyacrylamide gels was examined using a hand-held long wavelength (approximately 340 nm) UV light (Gelman Sciences).

Enrichment Cultures

The phosphodiester hydrolysis products of phosphotriesterases can be used as phosphorus sources by a wide range of bacteria (Cook et al., 1978; Rosenberg and Alexander, 1979). An enrichment culture was therefore established in which 1 g of soil obtained from a domestic yard, which had previously been exposed to diazinon (a diethyl thion OP), served as an inoculum for 50 ml enrichment medium (Table 2), in which coumaphos was the only added phosphorus source.

TABLE 2

Composition of coumaphos enrichment media.

| Medium (per liter) | | Trace element solution (per liter) | |
|---|---|---|---|
| Tris | 6.05 g | $(NH_4)_6Mo_7O_{24} \cdot 4H_2O$ | 20 mg |
| $NH_4Cl$ | 1 g | $H_3BO_3$ | 50 mg |
| $FeCl_2$ | 20 µg | $ZnCl_2$ | 30 mg |
| KCl | 0.5 g | $CoCl_2 \cdot 6H_2O$ | 3 mg |
| Sodium acetate | 0.68 g | $MnCl_2 \cdot 4H_2O$ | 10 mg |
| $MgSO_4$ | 0.1 g | Cupric acetate | 10 mg |
| p-aminobenzoate | 0.9 mg | | |
| nicotinic acid | 0.9 mg | | |
| Trace element solution | 10 ml | | |
| Coumaphos | 100 mM | | |
| pH 7.0 | | | |

Ten percent of the enrichment culture was subcultured twice into 50 ml fresh enrichment medium containing coumaphos as the sole phosphorus source. Coumaphos was then replaced with diazinon (at 100 mM) in the enrichment medium and the culture subcultured as before. After 3 days incubation at 28° C., the enrichment culture was further subcultured into media in which 100 mM parathion (another diethyl thion OP) was the sole phosphorus source. It was noted that after two days the culture had turned yellow (presumably due to the production of p-nitrophenol). This culture was then diluted in phosphorus-free medium and plated onto low salt LB plates (10 g/l tryptone, 5 g/l yeast extract and 2.5 g/l NaCl). After three days of growth at 28° C., approximately 100 colonies were picked randomly, re-streaked to ensure purity and then assayed for coumaphos hydrolytic activity using the microtitre plate assay described above. Fluorescence was measured after 8 hours at room temperature. One isolate (designated P230) demonstrated significant fluorescence and this isolate was examined further. Colonies of this isolate also demonstrated fluorescence on an agar plate containing coumaphos.

Example 2

Identification of Isolate P230

Isolate P230 was a Gram negative, catalase positive and oxidase positive, rod-shaped bacterium. To determine the identity of isolate P230, sequence analysis of the 16S rRNA gene was performed. DNA was extracted from isolate P230 according to the method of Rainey et al. (1992). Cells of a P230 culture that had been grown in low salt LB medium (2 ml) overnight at 28° C. were pelleted by centrifugation in a microfuge (12 000 rpm/2 minutes). The cell pellet was resuspended in 400 µl STE buffer (10 mM Tris-HCl, 100 mM NaCl, 1 mM EDTA, pH8.0) and 5 µl of a freshly-prepared lysozyme solution (0.3 µg/µl) was added. After incubation at 37° C. for 20 minutes, Proteinase K (15 µl of a 1% solution) and SDS (10 µl of a 25% solution) were added and the reactions incubated at 60° C. for 30 minutes. DNA preparations were then extracted sequentially with an equal volume of buffer-saturated phenol, and then an equal volume of chloroform.

The 16S rRNA gene was amplified from the extracted DNA by PCR using bacterial universal primers 27f (5' AGAGTTTGATCMTGGCTCAG 3') (SEQ ID NO: 9) and 1492r (5' TACGGYTACCTTGTTACGACTT 3') (SEQ ID NO: 10), the names of which are based on the numbering system of the *E. coli* 16S rRNA gene (Lane, 1991). Approximately 1320 bp of the 16S rRNA gene from isolate P230 was obtained and sequence similarities were performed using the FASTA algorithm (Pearson and Lipman, 1988). The 16S rRNA gene of isolate P230 was very similar in sequence to that of other *Agrobacterium* strains (Table 3).

TABLE 3

Nucleic acid sequence comparisons of the 16S rRNA genes of isolate P230 with those of various *Agrobacterium* strains.

| *Agrobacterium* strains | Sequence Identity (%) |
|---|---|
| *Agrobacterium radiobacter* LMG383 | 100 |
| *Agrobacterium* sp LMG11936 | 99.7 |
| *Agrobacterium* sp. MSMC211 | 99.5 |
| *Agrobacterium* sp. LMG11915 | 99.3 |

These results suggested that isolate P230 was an *Agrobacterium* strain. The utilization of carbon sources by isolate P230 was examined using the Biolog system (Oxoid), according to procedures recommended by the manufacturer. The carbon utilization profile was then compared with that of known species of *Agrobacterium* (Table 4; Krieg and Holt, 1984). The isolate was capable of using sucrose, ornithine and glucose as carbon sources. This, along with a positive oxidase reaction determined using Kovac's method (Kovac, 1956), suggested that the isolate was most similar to either *A. tumefaciens* biovar1 or *A. radiobacter* biovar1.

TABLE 4

Carbon utilization profiles and oxidase status of isolate P230 and known *Agrobacterium* species.

| | *Agrobacterium* spp. | | | | | | |
|---|---|---|---|---|---|---|---|
| Carbon source/ test | *A. tumefaciens* biovar1 | *A. tumefaciens* biovar2 | *A. radiobacter* biovar1 | *A. radiobacter* biovar2 | *A. rhizogenes* biovar2 | *A. rubi* | Isolate P230 |
| Tween 80 | − | − | − | − | − | − | − |
| Sucrose | + | − | + | − | − | − | + |
| Ornithine | + | + | + | + | + | + | + |
| D-glucose | + | + | + | + | + | + | + |

TABLE 4-continued

Carbon utilization profiles and oxidase status of isolate P230 and known *Agrobacterium* species.

| Carbon source/ test | *Agrobacterium* spp. | | | | | | |
|---|---|---|---|---|---|---|---|
| | *A. tumefaciens* biovar1 | *A. tumefaciens* biovar2 | *A. radiobacter* biovar1 | *A. radiobacter* biovar2 | *A. rhizogenes* biovar2 | *A. rubi* | Isolate P230 |
| Oxidase test (Kovac) | + | − | + | − | − | − | + |

*A. tumefaciens* biovar1 and *A. radiobacter* biovar1 can be distinguished by the presence of a tumour-inducing plasmid in the former. The tumour-inducing ability of strain P230 was tested in a tomato seedling by transferring a heavy suspension of bacteria in water to the leaves and using a sterile needle to pierce the surface of the leaves through the suspension. No evidence of tumours was seen after a period of four weeks. *A. tumefaciens* C58 was used as a positive control and produced tumours in this period of time. A cured strain of *A. tumefaciens* C58 was used as a negative control and produced the same effects in the test plant as isolate P230. Therefore isolate P230 was designated as a strain of *Agrobacterium radiobacter* biovar1.

Example 3

Constitutive Expression of Coumaphos Hydrolytic Activity

In order to determine if the phosphotriesterase activity of *A. radiobacter* P230 was constitutively expressed, regardless of the presence of OPs, the parathion hydrolytic activities of cultures of *A. radiobacter* P230 were examined in the presence and absence of parathion (Table 5). Growth was monitored by measuring the optical density of the cultures at 595 nm in a BioRad Model 3550-UV microplate spectrophotometer. Parathion hydrolytic activity was assayed according to the procedure of Serdar et al. (1989). This involved measuring the formation of p-nitrophenol from parathion at 405 nm in a BioRad Model 3550-UV microplate spectrophotometer. The reaction mixture contained 880 µM parathion in 50 mM Tris-HCl pH8.0 (this reaction also contained 5% methanol). Table 5 shows that parathion hydrolytic activity was constitutively expressed in isolate P230 and that the majority of this activity was expressed in early- to mid-log phase.

Example 4

Native Polyacrylamide Gel Electrophoresis (PAGE) of P230 Extracts

To demonstrate that a single enzyme was involved in coumaphos hydrolysis, native gels of *A. radiobacter* P230 cell extracts were stained for coumaphos hydrolytic activity. A culture (50 ml) of *A. radiobacter* P230 in low salt LB broth was pelleted by centrifugation at 8000 g for 15 minutes and the cell pellet resuspended in 2 ml 50 mM Tris-HCl pH8.0. Cells were disrupted by sonication (five 15 second bursts at 4° C.) and large cell debris or intact cells removed by centrifugation (8000 g for 15 minutes). An aliquot of the resultant supernatant (containing 5 µg protein) was then separated on a 10% (29:1 acrylamide:bis) SDS-PAGE gel. Prior to loading, neither SDS nor β-mercaptoethanol was added to the sample and furthermore, the sample was not boiled as in conventional SDS-PAGE. After electrophoresis the gel was equilibrated for 5 min in 50 mM Tris-HCl pH8.0, and then incubated for a further 5 min in 50 mM Tris-HCl pH8.0, containing 8 µM coumaphos. The gel was then examined under UV light as described above. A major fluorescent band was detected, indicating that the P230 isolate contains a single enzyme with coumaphos hydrolytic activity. This enzyme had an apparent molecular mass of 66 kDa.

TABLE 5

Parathion hydrolytic activities of P230 cultures grown in the presence or absence of parathion to an OD at 595 nm of 0.280.

| Culture | Parathion hydrolytic activity (µmol/min/mg protein) |
|---|---|
| +parathion | 3.36 ± 0.18 |
| −parathion | 3.13 ± 0.07 |

Example 5

Cloning the Gene Responsible for Coumaphos Hydrolytic Activity

Cloning Techniques and DNA Preparations

General cloning techniques, unless otherwise indicated, were standard and as described by Sambrook et al. (1989). Chromosomal DNA was extracted from *A. radiobacter* P230 according to the method of Gardiner et al. (1996). Briefly, an overnight culture (100 ml) of *A. radiobacter* P230 was pelleted by centrifugation at 5000 g for 20 minutes, washed twice with 10 ml ice-cold STE buffer (see above), and finally resuspended in 10 ml STE. Lysozyme (20 mg) was added and the cells incubated for 2 hours at 37° C. An equal volume of STE was added along with SDS (to a final concentration of 2% [w/v]) and RNase (to a final concentration of 20 µg/ml) and the cell lysate incubated at 42° C. for 1 hour. Proteinase K (50 µg/ml final concentration) was then added and the lysate incubated at 55° C. until the solution became translucent. An equal volume of buffer-saturated phenol/chloroform (1:1) was added, the sample thoroughly mixed and then centrifuged at 5000 g for 1 hour at 4° C. The upper aqueous layer was transferred to a clean tube using a broken pipette in order to prevent shearing of DNA. To precipitate the chromosomal DNA, 3M sodium acetate, pH5.2, (0.1 volume) and ice-cold ethanol (2.5 volumes) were added, the solution mixed gently and placed at −20° C. for 1 hour. The DNA was then removed using a "hooked" pasteur pipette. This precipitate was washed with 70% ethanol and air-dried for 5 minutes. TE buffer (pH8.0; 1 ml) was added and the DNA left to dissolve at 4° C. overnight.

Library Construction in *E. coli*

A partial Sau3AI digest of *A. radiobacter* P230 chromosomal DNA was prepared by digesting 37.5 µg of DNA with 4, 2, 1, 0.5 and 0.25 units of Sau3AI restriction endonuclease for 10 minutes at 37° C. DNA fragments in the size range of 10-12 kb were excised from a 0.7% agarose gel and extracted using a QIAGEN PCR purification/gel extraction kit, according to the manufacturer's instructions. pBluescript KS+ plasmid DNA (Stratagene), prepared using the Geneworks Ultraclean Plasmid miniprep kit, was digested with BamHI for 1 hour at 37° C. and dephosphorylated using calf intestinal alkaline phosphatase (Boehringer Mannheim). The phosphatase was then removed using the QIAquick PCR purification kit (QIAGEN). The size-fractionated P230 DNA fragments were ligated to the BamHI digested, phosphatase treated pBluescript vector, using T4 DNA ligase and the T4 ligase buffer provided by New England Biolabs. Ligations were performed for 20 hours at 4° C.

The ligated DNA was then transformed into *E. coli* DH10β using the revised Hanahan transformation method (Sambrook et al., 1989). The transformation mix was plated onto LB agar plates containing ampicillin (100 µg/ml), X-Gal (5-bromo-4-chloro-3-indolyl-β-D-galactoside; 40 µg/ml) and IPTG (isopropyl-β-D-thiogalactoside; 40 µg/ml), and incubated at 37° C. overnight. Approximately 350 white colonies were revealed.

Triparental Matings for Expression in *A. tumefaciens*

Since it was possible that the gene encoding the OP hydrolytic activity in *A. radiobacter* would not be expressed sufficiently in *E. coli* to allow identification on the basis of expression, the pBluescript plasmids from the *E. coli* library above were transferred into a closely-related strain, *A. tumefaciens* C58. *A. tumefaciens* C58 is a non-OP hydrolysing strain of *Agrobacterium* (Zimmerer at al., 1966). Briefly, the white colonies identified above on LB plates containing ampicillin, X-Gal and IPTG were patched onto LB plates, without any additions. Also patched onto the same plates at the same places were *A. tumefaciens* C58 and *E. coli* JM109 (Yanisch-Perron et al., 1985) containing the conjugative, cointegrative plasmid, pR751::Tn813 (Bowen and Pemberton, 1985). It was intended that the conjugative cointegrative plasmid would move into *E. coli* DH10β containing the pBluescript-derivatives and form a cointegrate. The cointegrates would then be transferred into *A. tumefaciens* C58.

The tri-parental matings were incubated overnight at 28° C. The mating mixtures were then scraped up and assayed for coumaphos hydrolytic activity in a microtitre plate. This involved resuspending the mating mix in an assay buffer containing 0.5% Triton X-100, 100 µM coumaphos and 50 mM Tris-HCl pH8.0. The microtitre plates were then incubated for 8 hours at room temperature, and the amount of fluorescence noted as described above. One mating mix (containing clone p65) demonstrated significant fluorescence.

Coumaphos Hydrolytic Activity of *E. coli* DH10β p65 Cell-Free Extracts

Cell-free extracts of *E. coli* DH10β p65, and control extracts containing the pBluescript vector alone, were prepared from cells grown to mid-log phase on LB medium containing ampicillin (100 µg/ml). The 50 ml cultures were pelleted by centrifugation at 8000 g for 15 minutes and resuspended in 2 ml 50 mM Tris-HCl pH8.0. The cells were disrupted by sonication (five 15 second bursts at 4° C.) and large cell debris or intact cells were removed by centrifugation (8000 g for 15 minutes). Aliquots (containing 15 µg protein) of the supernatants were assayed for coumaphos hydrolytic activity. The increase in fluorescence over time was measured and the amount of activity determined. It can be seen from Table 6 that cell-free extracts of *E. coli* DH10β containing clone p65 displayed significant coumaphos hydrolytic activity compared to that of the vector-only controls.

Localisation of the Gene Encoding the OP Hydrolytic Activity in Clone p65

Clone p65 DNA was digested to completion with HindIII and the resultant four fragments [5.5 kb (containing pBluescript vector), 4 kb, 3.5 kb and 1.4 kb] separated and subsequently excised from a 1% agarose gel. The fragments were extracted using the QIAquick PCR purification kit (QIAGEN) and ligated to HindIII digested pBluescript DNA prepared as described above. The ligation mixes were transformed into *E. coli* DH10β and individual clones assayed for coumaphos hydrolytic activity. Several of the clones containing the 4 kb HindIII fragment demonstrated coumaphos hydrolytic activity, depending on the orientation of the fragment in pBluescript relative to the lac promoter.

TABLE 6

Coumaphos hydrolytic activity of cell-free extracts of *E. coli* DH10β p65 and control extracts containing the pBluescript vector alone.

| Strain | Coumaphos hydrolytic activity (nmol/min/mg protein) |
|---|---|
| *E. coli* DH10β (pBluescript) | 0.78 ± 0.04 |
| *E. coli* DH10β (p65) | 3.30 ± 0.07 |

Example 6

Sequence of opdA

The nucleotide sequence of the 4 kb HindIII fragment identified above was determined using primers complementary to the T3 and T7 promoters in the vector and 'primer walking'. DNA was sequenced using the BigDye Terminator system (Applied BioSystems) on the Applied BioSystems ABI PRISM 377 automated DNA sequencer. An open reading frame (ORF) was identified in the same orientation as the lacZ promoter in clones possessing activity and in the opposite orientation in clones lacking activity. The open reading frame contains 1152 nucleotides (FIG. 2) and, when translated, would encode a protein of 384 amino acids (FIG. 3) and 41.4 kDa.

Sequence similarities were calculated using the FASTA algorithm (Pearson and Lipman, 1988). This indicated that the ORF had 88% nucleotide sequence identity to opd, a previously identified phosphotriesterase gene from *Flavobacterium* sp. ATCC27551 (Mulbry and Karns, 1989). Furthermore, the inferred amino acid sequence of the ORF was 90% identical to that of the *Flavobacterium* OPD enzyme (FIG. 4). For this reason we have named this open reading frame 'opdA'.

Some notable differences were observed between the *Flavobacterium* opd sequence and that of opdA from *A. radiobacter* P230 (FIGS. 2 and 3). There appears to be one less amino acid in the putative signal sequence of the OpdA protein and the signal cleavage site is also different. Furthermore, a frameshift near the 3' end of the opdA gene gives OpdA an additional 16 amino acids. This region has been sequenced multiple times to ensure that the extra base in opdA is not a sequencing error.

The native OPD enzyme is a homodimer that contains two zinc ions per monomeric subunit (Benning et al., 1995). The two His residues at positions 254 and 257 in the OPD protein sequence are located near the bimetallic active site present in each monomer and are thought to interact with active site residues and the substrate in the substrate binding pocket. Replacement of each of these His residues with Arg and Leu, respectively, resulted in enzymes possessing only two metal atoms per dimer (diSioudi et al., 1999). The OpdA protein has Arg and Tyr at the positions corresponding to His 254 and His257 in OPD (FIG. 4). It would therefore be expected that the OpdA native enzyme would contain only two metal ions per dimer rather than four, as in native OPD.

Example 7

Activity of the Purified OpdA Protein

To confirm that the open reading frame in FIG. 3 encoded the protein responsible for OP hydrolytic activity, the protein was expressed and purified as a fusion protein with maltose-binding protein.

Expression of OpdA and OPD as Fusion Proteins

The OpdA and OPD proteins were expressed in *Escherichia coli* using the pMAL protein fusion and purification system of New England Biolabs, which results in the expression of maltose-binding protein (MBP) fusion proteins.

To clone the opdA gene into the pMAL-c vector, the opdA gene (without the signal peptide domain) was amplified by the polymerase chain reaction (PCR) using the upstream and downstream primers, 5'GATCGT CTGCAGCCAATCGGTACAGGCGATCTG (SEQ ID NO: 11) and 5'GATCGT AAGCTTTCATCGTTCGGTATCTTGACGGGGAAT (SEQ ID NO: 12), respectively. A PstI cloning site was inserted at the start codon and a HindIII cloning site at the stop codon (underlined bases). The PCR fragment was subsequently cloned into the PstI-HindIII cloning sites of pMAL-c, to generate the recombinant plasmid, pmal-opdA.

The opd gene (Mulbry and Karns, 1989) was cloned into the pMAL-c2× vector (New England Biolabs) in a similar way. The opd gene, without the signal peptide domain, was amplified using PCR. The upstream and downstream oligonucleotide primers, 5'GATCGT GGATCCTCGATCGGCACAGGCGATCGG (SEQ ID NO: 13) and 5'GATCGT AAGCTTTCATGACGCCCGCAAGGTCGG (SEQ ID NO: 14), respectively, were designed to contain a BamHI restriction site at the opd start codon and a HindIII restriction site at the stop codon (underlined bases). The PCR fragment was subsequently cloned into the BamHI-HindIII restriction sites of pMAL-c2× to generate the recombinant plasmid, pFmal.

Purification of OpdA and OPD Proteins

Both MBP fusion proteins were expressed in *E. coil* DH10β cells. Optimal production of MBP fusion proteins was obtained when mid-log cells ($OD_{600}$=0.6) were induced with 0.1 mM isopropyl-β-D-thiogalactopyranoside for 5 hours at 37° C. Harvested cells were disrupted by sonication and the soluble fraction loaded onto an amylose resin (New England Biolabs), equilibrated with 50 mM Tris-HCl pH7.5. MBP fusion proteins were eluted with 10 mM maltose in 50 mM Tris-HCl pH7.5. Fractions containing coumaphos hydrolytic activity were pooled and cleaved with Xa protease (10 μg/ml; New England Biolabs) for 5 hours. The cleaved fractions were then passaged through a DEAE sepharose ion exchange resin. Cleaved OpdA and OPD proteins did not bind to this resin and eluted with the void volume. Fractions from this sample appeared to be pure as judged by SDS-PAGE. The amount of protein in purified samples was calculated according to the method of Gill and von Hippel (1989).

Kinetic Analyses of OPD and OpdA (i) Substrates

Kinetic parameters were determined for the hydrolysis by OpdA and OPD of the following substrates: coumaphos, parathion (O,O-diethyl p-nitrophenyl phosphorothioate; Riedel de Haan), parathion-methyl (O,O-dimethyl p-nitrophenyl phosphorothioate; Riedel de Haan), paraoxon (O,O-diethyl p-nitrophenyl phosphate; Sigma), coroxon (3-chloro-4-methyl-7-coumarinyl diethyl phosphate; Alltech), fenthion (O,O-dimethyl O-[3-methyl 4-(methylthio)phenyl]phosphorothioate; Riedel de Haan), diazinon (labelled—O,O-diethyl-O-(2-isopropyl-4-methyl-6-pyrimidinyl)-phosphorothioate; Alltech), dMUP (O,O-dimethyl 4-methyl-umbelliferyl phosphate; a gift from Alan Devonshire), chlorpyrifos (O,O-diethyl O-3,5,6-trichloro-2-pyridyl phosphorothioate; Alltech) and phosmet (S-[(1,3-dihydro-1,3-dioxo-2H-isoindol-2-yl) methyl O,O-dimethyl phosphorodithioate; Alltech).

(ii) Assays

All reactions contained organophosphates dissolved in methanol, except for phosmet, which was dissolved in acetone. The concentration of acetone or methanol in the reactions was constant at 5%, where appropriate. All reactions were performed in 50 mM Tris-HCl pH 8.0 at 25° C.

The initial rates of reactions of purified OPD and OpdA with coumaphos and coroxon were determined using the fluorimetric assay described above.

The initial rates of reaction of both OPD and OpdA with dMUP were determined using a fluorimetric assay to quantitate the formation of the hydrolysis product, 4-methyl umbelliferone (Roth, 1969). The fluorescence was measured using an excitation wavelength of 355 nm and an emission intensity of 460 nm.

The initial rates of reaction of both purified enzymes with parathion, parathion-methyl and paraoxon were measured spectrophotometrically by quantitating the formation of the hydrolysis product, p-nitrophenol, at 405 nm and using an extinction coefficient of 17 000 $M^{-1}cm^{-1}$ (Dumas et al., 1989b).

The initial rates of reaction of OpdA with fenthion were quantitated spectrophotometrically by monitoring a reduction in absorbance at 252 nm (Ibrahim and Cavagnol, 1966). A lack of hydrolysis of fenthion and phosmet by OPD was confirmed by thin layer chromatography after 24 hour incubation of the substrate with OPD.

The reaction rates of OpdA and OPD with chlorpyrifos were measured spectrophotometrically by monitoring the increase in absorbance at 276 nm (Dumas et al., 1989b).

The hydrolysis of phosmet was measured by quantitating the formation of free thiols during the course of the reaction using DTNB (Ellman's reagent; 5'5 dithio-bis-(2-nitro benzoic acid)) as has been described previously for monitoring P—S hydrolysis in organophosphates (Lai et al., 1995). This involved the addition of DTNB (80 μl of 1 mg/ml in 50 mM sodium phosphate pH7.5 and methanol, 1:1 (v/v)) to 20 μl aliquots of the reaction taken at various times.

The hydrolysis of diazinon was monitored using radiolabelled diazinon (ethyl-1-$^{14}$C; 14.8 MBq/mmol) in the radiometric partition assay previously used for radiolabelled OP substrates (Campbell et al., 1998). At various times during the reaction, an aliquot (50 μl) was removed and diluted with 150 μl water. This was then extracted with 500 μl dichloromethane. The upper aqueous phase (150 μl) was removed and quantitated by liquid scintillation.

Results

Results of the kinetic analyses are given in Table 7. OpdA and OPD were able to hydrolyse the substrates coumaphos, coroxon, paraoxon, parathion, parathion-methyl, diazinon, chlorpyrifos and dMUP. OpdA had a higher $k_{cat}$ for both parathion-methyl and dMUP, and OPD was unable to hydrdolyse either phosmet or fenthion. A lack of hydrolysis of the latter two substrates was also observed over a 24 hour period by thin layer chromatography (Munnecke and Hsieh, 1976). This involved the extraction of a 100 µl reaction containing 0.4 mM substrate with an equal volume of ethyl acetate. The upper organic phase was gently dried with a nitrogen stream, and the remaining residue was dissolved in 10 µl acetone and then applied to a neutral silica gel $F_{254}$ TLC plate (Alltech, NSW, Australia). The plate was then developed in hexane-chloroform-methanol (7:2:1) and compounds visualised by short wavelength ultra-violet light. Hydrolysis of both phosmet and fenthion were consistently observed for OpdA and no hydrolysis was seen for OPD.

In summary, several differences in substrate specificity between OpdA and OPD were observed. OpdA hydrolysed fenthion and phosmet whereas OPD did not. Furthermore, there was a significant difference between OpdA and OPD in the $k_{cat}$ values for dimethyl OPs, with OpdA possessing a higher $k_{cat}$ for methyl-parathion and dMUP than OPD. We would also expect OpdA, like OPD (Dumas et al., 1989a; Yang et al, 1995), to hydrolyse OP nerve agents.

As discussed above, the two His residues at positions 254 and 257 in the OPD protein sequence are located near the bimetallic active site present in each monomer and are thought to interact with active site residues and the substrate in the substrate binding pocket (Benning et al., 1995). Replacement of each of these His residues with Arg and Leu, respectively, resulted in enzymes with only one metal ion per monomer, increased catalytic activity for larger substrates such as demeton, and decreased activity for smaller

TABLE 7

Kinetic parameters of purified OpdA and OPD enzymes for various OP substrates.

| Substrate/Structure | $K_m$ (µM) | | $k_{cat}$ (min$^{-1}$) | |
|---|---|---|---|---|
| | OpdA | OPD | OpdA | OPD |
| coumaphos | 8.3 ± 1.8 | 21.4 ± 6.0 | 12.4 ± 0.6 | 14.1 ± 2.6 |
| coroxon | 15.9 ± 1.9 | 25.3 ± 1.3 | 22.7 ± 0.1 | 39.5 ± 5.3 |
| paraoxon | 242 ± 61 | 225 ± 14 | 33.5 ± 0.5 | 46.0 ± 0.4 |
| parathion | 92.6 ± 6.4 | 50.6 ± 12.2 | 21.9 ± 2.0 | 23.5 ± 0.2 |
| parathion-methyl | 61.2 ± 2.3 | 32.9 ± 1.7 | 94.2 ± 0.8 | 5.46 ± 0.05 |

TABLE 7-continued

Kinetic parameters of purified OpdA and OPD enzymes for various OP substrates.

| Substrate/Structure | $K_m$ (μM) OpdA | $K_m$ (μM) OPD | $k_{cat}$ (min⁻¹) OpdA | $k_{cat}$ (min⁻¹) OPD |
|---|---|---|---|---|
| phosmet | 208.3 ± 13.2 | — | 0.100 ± 0.002 | — |
| fenthion | 148.6 ± 17.2 | — | 1.63 ± 0.01 | — |
| diazinon | 51.9 ± 4.5 | 54.2 ± 5.4 | 65.2 ± 6.7 | 56.5 ± 2.9 |
| chlorpyrifos | 32.6 ± 8.1 | 47.2 ± 3.0 | 0.525 ± 0.005 | 0.90 ± 0.01 |
| dMUP | 66.0 ± 9.1 | 46.7 ± 2.8 | 81.7 ± 9.1 | 20.5 ± 2.3 |

. . . /cont.

substates like paraoxon (diSioudi et al., 1999). It was postulated that changes in the number of bound metal ions may enhance structural flexibility and improve access of larger substrates to the active site, while simultaneously decreasing activity for smaller substrates. The OpdA protein has Arg and Tyr at the positions corresponding to His 254 and His257 in OPD (FIG. 4). It is therefore surprising that OpdA possessed a higher $k_{cat}$ for methyl-parathion than OPD, yet its $k_{cat}$ for the larger ethyl-parathion substrate was similar to that of OPD. Similar results were obtained for the coumaphos/dMUP substrate pair. Clearly, differences between the OpdA and OPD amino acid sequences other than those at residues 253/254 and 256/257 affect catalytic activity.

Example 8

Identification of OpdA Mutants with Altered Specificity

The plasmid pmal-opdA was transformed into the *E. coli* mutator strain XL1-red. The plasmid was propagated in this strain for 120 generations, with plasmid extractions occurring after every 24 generations. These plasmids were then transformed into *E. coli* DH1013 and the transformation mix diluted to 50 ml in LB containing ampicillin.

When the culture reached an $OD_{595}$ of 0.3, fusion protein expression was induced with 0.1 mM IPTG, and induction allowed to occur for 5 hours. The culture was then pelleted by centrifugation, resuspended in 2 ml of sterile 50 mM Tris-HCl pH7.5 with the addition of malathion to a final concentration of 440 µM. This assay mixture was left for 1 hour and the hydrolysis of malathion detected using Ellman's reagent (DTNB) (Lai et al., 1995).

Pools containing activity were then diluted and plated onto LB plates with ampicillin. Individual colonies were then selected and tested for malathion and dimethoate hydrolytic activity as described above. Two colonies (designated pmal-opdA1 and pmal-opdA2) were selected and examined further.

The sequences of the two mutants were examined and compared with that of wild-type OpdA. OpdA1 contained 4 mutations (P42S, P134S, A170S and S237G) (SEQ ID NO: 3) and OpdA2 contained one mutation (A119D) (SEQ ID NO: 4). The numbering system is based on OpdA numbering of amino acid residues, taking into account the signal sequence. To correlate the numbering with OPD, add one to each number.

OpdA and the two mutants OpdA1 and OpdA2 were purified after expression in the plasmid pCY76. The genes were amplified by PCR using the primers pETopdA5 (5'GATCGT GAATTCCATATGCCAATCGGTACA, with EcoRI site underlined and NdeI double underlined) (SEQ ID NO: 15) and pETopdA3 (5'GATCGT GGATCCTCATCGTTCGGTATCTTG, with BamHI site underlined) (SEQ ID NO:16). PCR fragments were digested with EcoRI and BamHI and ligated with similarly-digested pBluescript. Sequence of the fragments were confirmed in this vector. The pBS-derivatives were then digested with NdeI-BamHI and ligated with NdeI-BglII-digested pCY76. Positive clones were grown in 500 ml of LB. After the cultures had grown for 24 hours, they were pelleted by centrifugation at 7000 g, 15 minutes at 4° C. The pellets were resuspended in 4 ml 50 mM Tis-HCl pH7.5 and broken by sonication (Harcourt et al., 2002). Cell-free extracts were then charged onto a DEAE sepharose column that was pre-equilibrated with 50 mM Tris-HCl pH7.5. OpdA and variants did not bind to this column and the eluant was collected and placed on a heparin sepharose column pre-equilibrated with 50 mM Tris-HCl pH7.5 (Pharmacia). OpdA and variants were bound by this column and eluted with 50 mM Tris-HCl pH7.5/0.1 M NaCl. After this column step, OpdA was judged to be pure by SDS-PAGE. The kinetics of the proteins were examined against the aliphatic OPs, dimethoate, malathion, malaoxon and DFP (diisopropyl fluorophosphate) (Table 8). Both mutants were active against dimethoate, malathion and malaoxon, whereas the wild-type OpdA was not. Furthermore, the mutants had increased activity for DFP compared to that of wild-type OpdA.

TABLE 8

The kinetic parameters of purified OpdA and the mutants, OpdA1 and OpdA2, for various OP substrates.

| Substrate | $K_m$ (µM) | | | $k_{cat}$ (min$^{-1}$) | | |
|---|---|---|---|---|---|---|
| | OpdA | OpdA1 | OpdA2 | OpdA | OpdA1 | OpdA2 |
| DFP | 2.3 ± 0.4 | 18.1 ± 0.6 | 9.6 ± 5.6 | 1.36 ± 0.04 | 45.9 ± 0.9 | 27.5 ± 0.7 |
| dimethoate | nd[1] | 78.9 ± 17.7 | 14.3 ± 4.2 | nd | 1.22 ± 0.07 | 1.4 ± 0.1 |
| malathion | nd | 33.3 ± 14.2 | 40.9 ± 7.2 | nd | 1.21 ± 0.07 | 1.43 ± 0.07 |
| malaoxon | nd | 159.2 ± 28.2 | 45.7 ± 8.9 | nd | 1.98 ± 0.05 | 1.84 ± 0.06 |

[1]nd = not detected

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

REFERENCES

Benning, M. M., Kuo, J. M., Raushel, F. M. and Holden, H. M. (1995). Biochemistry 34: 7973-7978.

Billecke, S. S., Primo-Parmo, S. L., Dunlop, C. S., Doorn, J. A., La Du, B. N. and Broomfield, C. A. (1999). Chemico-Biological Interactions 120: 251-256.

Bowen, A. R. StG. and Pemberton, J. M. (1985). Mercury resistance transposon Tn813 mediates chromosome transfer in Rhodopseudomonas sphaeroides and intergeneric transfer in pBR322. In Helsinki, D. R., S. N. Cohen, D. B. Clewell, D. A. Jackson and A. Hollaender (ed.), Plasmids in Bacteria. Plenum Press, New York, p 105-115.

Broomfield, C. A., Lockridge, O. and Millard, C. B. (1999). Chemico-Biological Interactions 119-120: 413-418.

Buchbinder, J. L., Stephenson, R. C., Dresser, M. J., Pitera, J. W., Scanlan, T. S. and Fletterick, R. J. (1998). Biochemistry 37: 5096-5160.

Campbell, P. M., Newcomb, R. D., Russell, R. J. and Oakeshott, J. G. (1998). Insect Biochemistry and Molecular Biology 28: 139-150.

Cheng, T., DeFrank, J. J. and Rastogi, V. K. (1999). Chemico-Biological Interactions 119-120: 455-462.

Claudianos, C., Russell, R. J. and Oakeshott, J. G. (1999). Insect Biochemistry and Molecular Biology 29: 675-686.

Cook, A. M., Daughton, C. G. and Alexander, M. (1978). Applied and Environmental Microbiology 36: 668-672.

Davies, J. A., Buchman, V. L., Krylova, O. and Ninkina, N. N. (1997). FEBS Letters 410: 378-382.

diSioudi, B., Grimsley, J. K., Lai, K. and Wild, J. R. (1999). Biochemistry 38: 2866-2872.

Doorn, J. A., Sorenson, R. C., Billecke, S. S., Hsu, C. and La Du, B. N. (1999). Chemico-Biological Interactions 120: 235-241.

Dumas, D. P., Wild, J. R. and Raushel, F. M. (1989a). Biotechnology and Applied Biochemistry 11: 235-243.

Dumas, D. P., S. R. Caldwell, J. R. Wild and F. M. Raushel. (1989b). Journal of Biological Chemistry 264: 19659-19665.

Dumas, D. P., Wild, J. R. and Raushel, F. M. (1990). Experientia 46: 729-731.

Gan, K. N., Smolen, A., Eckerson, H. W. and Bert, N. L. (1991). Drug Metabolism and Disposition 19: 100-106.

Gardiner, A. T., MacKenzie, R. C., Barrett, S. J., Kaiser, K. and Cogdell, R. J. (1996). Photosynthesis Research 49: 223-235.

Gill, S. C. and von Hippel, P. H. (1989). Analytical Biochemistry 182: 319-326.

Gordon, R. K., Feaster, S. R., Russell, A. J., LeJeune, K. E., Maxwell, M. D., Lenz, D. E., Ross, M. and Doctor, B. P. (1999). Chemical-Biological Interactions 14: 463-470.

Harcourt, R. L., Home, I., Sutherland, T. D., Hammock, B. D., Russell, R. J. and Oakeshott, J. G. (2002) Lett. Appl. Microbiol. 34: 263-268.

Harper, L. L., McDaniel, S., Miller, C. E. and Wild, J. R. (1988). Applied and Environmental Microbiology 54: 2586-2589.

Hong, S. B. and Raushel, F. M. (1999). Chemico-Biological Interactions 120: 225-234.

Hoskin, F. C. G., Walker, J. E. and Mello, C. M. (1999). Chemico-Biological Interactions 120: 399-404.

Ibrahim, F. B. and Cavagnol, J. C. (1966). Journal of Agricultural and Food Chemistry 14: 369-371.

Kovac, N. (1956). Nature 178: 703.

Krieg, N. R. and Holt, J. G. (ed.) 1984. Bergey's Manual of Determinative Bacteriology. The Williams & Wilkins Co., Baltimore.

Lai, K., Stolowich, N. J. and Wild, J. R. (1995). Archives of Biochemistry and Biophysics 318: 59-64.

Lane, D. J. (1991). 16S/23S rRNA sequencing, p 115-175. In E. Stackebrandt and M. Goodfellow (ed.) Nucleic acid techniques in bacterial systematics. John Wiley & Sons, New York.

LeJuene, K. E., Wild, J. R. and Russell, A. J. (1998). Nature 395: 27-28.

Mulbry, W. W. (1992) Gene 121: 149-153.

Mulbry, W. W. and Karns, J. S. (1989). Journal of Bacteriology 171: 6740-6746.

Mulbry, W. W. and Kearney, P. C. (1991). Crop Protection 10: 334-345.

Munnecke, D. M. and Hsieh, D. P. (1976). Applied and Environmental Microbiology 31: 63-69.

Newcomb, R. D., Campbell, P. M., Ollis, D. L., Cheah, E., Russell, R. J. and Oakeshott, J. G. (1997). Proceedings of the National Academy of Sciences USA 94: 7464-7468.

Pearson, W. R. and D. J. Lipman. (1988). Proceedings of the National Academy of Sciences USA 85: 2444-2448.

Petrikovics, I., Cheng, T. C., Papahadjopoulos, D., Hong, K., Yin, R., DeFrank, J. J., Jaing, J., Zong, Z. H., McGuinn, W. D., Sylvester, D., Pei, L., Madec, J., Tamulinas, C., Jaszberenyi, J. C., Barcza, T. and Way, J. L. (2000a). Toxicology Science 57: 16-21.

Petrikovics, I., McGuinn, W. D., Sylvester, D., Yuzapavik, P., Jaing, J., Way, J. L., Papahadjopoulos, D., Hong, K., Yin, R., Cheng, T. C., and DeFrank, J. J. (2000b). Drug Delivery 7: 83-89.

Rainey, F. A., M. Dorsch, H. W. Morgan and E. Stackebrandt. (1992). Systematic and Applied Microbiology 15: 197-202.

Rekha, M., Thakur, M. S., and Karanth, N. G. (2000). Critical Reviews in Biotechnology 20: 213-235.

Rosenberg, A. and Alexander, M. (1979). Applied and Environmental Microbiology 37: 886-891.

Roth, M. (1969). Methods of Biochemical Analysis 17: 189-285.

Sambrook, Fritsch, J. E. F. and Maniatis, T. (1989). Molecular cloning—A laboratory Manual. $2^{nd}$ Ed. Cold Spring Harbour Laboratory Press, USA.

Scanlen, C. S. and Reid, R. C. (1995). Chemistry and Biology 2: 71-75.

Serdar, C. M., Murdock, D. C. and Rohde, M. F. (1989). Bio/Technology 7: 1151-1155.

Sorenson, R. C., Primo-Parmo, S. L., Kuo, C-L, Adkins, S., Lockridge, O and La Du, B. N. (1995). Proceedings of the National Academy of Science USA 92: 7187-7191.

Wang, Q., Sun, M., Zhang, H. and Huang, C. (1998). Journal of Biochemistry and Molecular Toxicology 12: 213-217.

Wang, F., Xiao, M. and Shaofeng, M. (1993). Journal of Biochemistry and Toxicology 8: 161-166.

Yang, F., Wild, J. R. and Russell, A. J. (1995). Biotechnology Progress 11: 471-474.

Yanisch-Perron, Vieira, C. J. and Messing, J. (1985). Gene 33: 103-119.

Zimmerer, R. P., Hamilton, R. H. and Pootjes, C. (1966). Journal of Bacteriology 92: 746-750.

The invention claimed is:

1. A host cell comprising a recombinant polynucleotide which encodes a polypeptide comprising amino acids whose sequence is at least 95% identical to the sequence set forth as SEQ ID NO:2 or a composition comprising the polypeptide recovered from the host cell.

2. The host cell or composition of claim 1, wherein the polypeptide comprises amino acids whose sequence is at least 97% identical to the sequence set forth as SEQ ID NO:2.

3. The host cell or composition of claim 1, wherein the polypeptide is a substitution mutant of the polypeptide comprising amino acids whose sequence is set forth as SEQ ID NO:2.

4. The host cell or composition of claim 1, wherein the polynucleotide comprises nucleotides whose sequence is at least 95% identical to the sequence set forth as SEQ ID NO:6.

5. The host cell or composition of claim 1, wherein the polynucleotide is comprised in a vector.

6. The host cell or composition of claim 5, wherein the vector is a plasmid vector.

7. The host cell or composition of claim 5, wherein the vector is integrated into one or more host cell chromosomes.

8. The host cell or composition of claim 1, wherein the host cell is a bacterial cell or a yeast cell.

9. The host cell or composition of claim 8, wherein the bacterial cell is *Salmonella* sp., *Escherichia* sp., *Bacillus* sp., or *Listeria* sp.

10. The host cell or composition of claim 8, wherein the bacterial cell is *Escherichia coli*.

11. The host cell or composition of claim 2, wherein the host cell is a bacterial cell or a yeast cell.

12. The host cell or composition of claim 11, wherein the bacterial cell is *Salmonella* sp., *Escherichia* sp., *Bacillus* sp., or *Listeria* sp.

13. The host cell or composition of claim 11, wherein the bacterial cell is *Escherichia coli*.

14. The host cell or composition of claim 3, wherein the host cell is a bacterial cell or a yeast cell.

15. The host cell or composition of claim 14, wherein the bacterial cell is *Salmonella* sp., *Escherichia* sp., *Bacillus* sp., or *Listeria* sp.

16. The host cell or composition of claim 14, wherein the bacterial cell is *Escherichia coli*.

17. A composition comprising the host cell of claim 1 and one or more acceptable carriers.

18. A composition comprising the host cell of claim 14 and one or more acceptable carriers.

19. A composition comprising the host cell of claim 15 and one or more acceptable carriers.

20. A composition comprising the host cell of claim 16 and one or more acceptable carriers.

21. A process for preparing a polypeptide comprising amino acids whose sequence is at least 95% identical to the sequence set forth as SEQ ID NO:2, the process comprising cultivating the host cell of claim 1 under conditions which allow production of the polypeptide, and extracting the polypeptide.

* * * * *

SEQUENCE LISTING

<160> NUMBER OF SEQ ID NOS: 17

<210> SEQ ID NO 1
<211> LENGTH: 384
<212> TYPE: PRT
<213> ORGANISM: Agrobacterium radiobacter

<400> SEQUENCE: 1

```
Met Gln Thr Arg Arg Asp Ala Leu Lys Ser Ala Ala Ile Thr Leu
1               5                   10                  15

Leu Gly Gly Leu Ala Gly Cys Ala Ser Met Ala Arg Pro Ile Gly Thr
                20                  25                  30

Gly Asp Leu Ile Asn Thr Val Arg Gly Pro Ile Pro Val Ser Glu Ala
                35                  40                  45

Gly Phe Thr Leu Thr His Glu His Ile Cys Gly Ser Ser Ala Gly Phe
        50                  55                      60

Leu Arg Ala Trp Pro Glu Phe Phe Gly Ser Arg Lys Ala Leu Ala Glu
65                  70                  75                  80

Lys Ala Val Arg Gly Leu Arg His Ala Arg Ser Ala Gly Val Gln Thr
                85                  90                  95

Ile Val Asp Val Ser Thr Phe Asp Ile Gly Arg Asp Val Arg Leu Leu
                100                 105                 110

Ala Glu Val Ser Arg Ala Ala Asp Val His Ile Val Ala Ala Thr Gly
                115                 120                 125

Leu Trp Phe Asp Pro Pro Leu Ser Met Arg Met Arg Ser Val Glu Glu
        130                 135                     140

Leu Thr Gln Phe Phe Leu Arg Glu Ile Gln His Gly Ile Glu Asp Thr
145                 150                 155                 160

Gly Ile Arg Ala Gly Ile Ile Lys Val Ala Thr Thr Gly Lys Ala Thr
                165                 170                 175

Pro Phe Gln Glu Leu Val Leu Lys Ala Ala Arg Ala Ser Leu Ala
                180                 185                 190

Thr Gly Val Pro Val Thr Thr His Thr Ser Ala Ser Gln Arg Asp Gly
                195                 200                 205

Glu Gln Gln Ala Ala Ile Phe Glu Ser Glu Gly Leu Ser Pro Ser Arg
        210                 215                     220

Val Cys Ile Gly His Ser Asp Asp Thr Asp Asp Leu Ser Tyr Leu Thr
225                 230                 235                 240

Gly Leu Ala Ala Arg Gly Tyr Leu Val Gly Leu Asp Arg Met Pro Tyr
                245                 250                 255

Ser Ala Ile Gly Leu Glu Gly Asn Ala Ser Ala Leu Ala Leu Phe Gly
                260                 265                 270

Thr Arg Ser Trp Gln Thr Arg Ala Leu Leu Ile Lys Ala Leu Ile Asp
        275                 280                     285

Arg Gly Tyr Lys Asp Arg Ile Leu Val Ser His Asp Trp Leu Phe Gly
        290                 295                     300

Phe Ser Ser Tyr Val Thr Asn Ile Met Asp Val Met Asp Arg Ile Asn
305                 310                 315                 320

Pro Asp Gly Met Ala Phe Val Pro Leu Arg Val Ile Pro Phe Leu Arg
                325                 330                 335

Glu Lys Gly Val Pro Pro Glu Thr Leu Ala Gly Val Thr Val Ala Asn
                340                 345                 350

Pro Ala Arg Phe Leu Ser Pro Thr Val Arg Ala Val Thr Arg Ser
                355                 360                 365
```

```
Glu Thr Ser Arg Pro Ala Ala Pro Ile Pro Arg Gln Asp Thr Glu Arg
    370                 375                 380

<210> SEQ ID NO 2
<211> LENGTH: 356
<212> TYPE: PRT
<213> ORGANISM: Agrobacterium radiobacter

<400> SEQUENCE: 2

Pro Ile Gly Thr Gly Asp Leu Ile Asn Thr Val Arg Gly Pro Ile Pro
1               5                   10                  15

Val Ser Glu Ala Gly Phe Thr Leu Thr His Glu His Ile Cys Gly Ser
            20                  25                  30

Ser Ala Gly Phe Leu Arg Ala Trp Pro Glu Phe Phe Gly Ser Arg Lys
        35                  40                  45

Ala Leu Ala Glu Lys Ala Val Arg Gly Leu Arg His Ala Arg Ser Ala
    50                  55                  60

Gly Val Gln Thr Ile Val Asp Val Ser Thr Phe Asp Ile Gly Arg Asp
65                  70                  75                  80

Val Arg Leu Leu Ala Glu Val Ser Arg Ala Ala Asp Val His Ile Val
                85                  90                  95

Ala Ala Thr Gly Leu Trp Phe Asp Pro Pro Leu Ser Met Arg Met Arg
            100                 105                 110

Ser Val Glu Glu Leu Thr Gln Phe Phe Leu Arg Glu Ile Gln His Gly
        115                 120                 125

Ile Glu Asp Thr Gly Ile Arg Ala Gly Ile Ile Lys Val Ala Thr Thr
    130                 135                 140

Gly Lys Ala Thr Pro Phe Gln Glu Leu Val Leu Lys Ala Ala Ala Arg
145                 150                 155                 160

Ala Ser Leu Ala Thr Gly Val Pro Val Thr Thr His Thr Ser Ala Ser
                165                 170                 175

Gln Arg Asp Gly Glu Gln Gln Ala Ala Ile Phe Glu Ser Glu Gly Leu
            180                 185                 190

Ser Pro Ser Arg Val Cys Ile Gly His Ser Asp Asp Thr Asp Asp Leu
        195                 200                 205

Ser Tyr Leu Thr Gly Leu Ala Ala Arg Gly Tyr Leu Val Gly Leu Asp
    210                 215                 220

Arg Met Pro Tyr Ser Ala Ile Gly Leu Glu Gly Asn Ala Ser Ala Leu
225                 230                 235                 240

Ala Leu Phe Gly Thr Arg Ser Trp Gln Thr Arg Ala Leu Leu Ile Lys
                245                 250                 255

Ala Leu Ile Asp Arg Gly Tyr Lys Asp Arg Ile Leu Val Ser His Asp
            260                 265                 270

Trp Leu Phe Gly Phe Ser Ser Tyr Val Thr Asn Ile Met Asp Val Met
        275                 280                 285

Asp Arg Ile Asn Pro Asp Gly Met Ala Phe Val Pro Leu Arg Val Ile
    290                 295                 300

Pro Phe Leu Arg Glu Lys Gly Val Pro Pro Glu Thr Leu Ala Gly Val
305                 310                 315                 320

Thr Val Ala Asn Pro Ala Arg Phe Leu Ser Pro Thr Val Arg Ala Val
                325                 330                 335

Val Thr Arg Ser Glu Thr Ser Arg Pro Ala Ala Pro Ile Pro Arg Gln
            340                 345                 350

Asp Thr Glu Arg
            355
```

<210> SEQ ID NO 3
<211> LENGTH: 384
<212> TYPE: PRT
<213> ORGANISM: Artificial Sequence
<220> FEATURE:
<223> OTHER INFORMATION: Mutant of OpdA

<400> SEQUENCE: 3

```
Met Gln Thr Arg Arg Asp Ala Leu Lys Ser Ala Ala Ile Thr Leu
1               5                  10                  15

Leu Gly Gly Leu Ala Gly Cys Ala Ser Met Ala Arg Pro Ile Gly Thr
                20                  25                  30

Gly Asp Leu Ile Asn Thr Val Arg Gly Ser Ile Pro Val Ser Glu Ala
            35                  40                  45

Gly Phe Thr Leu Thr His Glu His Ile Cys Gly Ser Ser Ala Gly Phe
    50                  55                  60

Leu Arg Ala Trp Pro Glu Phe Phe Gly Ser Arg Lys Ala Leu Ala Glu
65                  70                  75                  80

Lys Ala Val Arg Gly Leu Arg His Ala Arg Ser Ala Gly Val Gln Thr
                85                  90                  95

Ile Val Asp Val Ser Thr Phe Asp Ile Gly Arg Asp Val Arg Leu Leu
            100                 105                 110

Ala Glu Val Ser Arg Ala Ala Asp Val His Ile Val Ala Ala Thr Gly
            115                 120                 125

Leu Trp Phe Asp Pro Ser Leu Ser Met Arg Met Arg Ser Val Glu Glu
    130                 135                 140

Leu Thr Gln Phe Phe Leu Arg Glu Ile Gln His Gly Ile Glu Asp Thr
145                 150                 155                 160

Gly Ile Arg Ala Gly Ile Ile Lys Val Ser Thr Thr Gly Lys Ala Thr
                165                 170                 175

Pro Phe Gln Glu Leu Val Leu Lys Ala Ala Arg Ala Ser Leu Ala
            180                 185                 190

Thr Gly Val Pro Val Thr Thr His Thr Ser Ala Ser Gln Arg Asp Gly
            195                 200                 205

Glu Gln Gln Ala Ala Ile Phe Glu Ser Glu Gly Leu Ser Pro Ser Arg
    210                 215                 220

Val Cys Ile Gly His Ser Asp Asp Thr Asp Asp Leu Gly Tyr Leu Thr
225                 230                 235                 240

Gly Leu Ala Ala Arg Gly Tyr Leu Val Gly Leu Asp Arg Met Pro Tyr
                245                 250                 255

Ser Ala Ile Gly Leu Glu Gly Asn Ala Ser Ala Leu Ala Leu Phe Gly
            260                 265                 270

Thr Arg Ser Trp Gln Thr Arg Ala Leu Leu Ile Lys Ala Leu Ile Asp
            275                 280                 285

Arg Gly Tyr Lys Asp Arg Ile Leu Val Ser His Asp Trp Leu Phe Gly
    290                 295                 300

Phe Ser Ser Tyr Val Thr Asn Ile Met Asp Val Met Asp Arg Ile Asn
305                 310                 315                 320

Pro Asp Gly Met Ala Phe Val Pro Leu Arg Val Ile Pro Phe Leu Arg
                325                 330                 335

Glu Lys Gly Val Pro Pro Glu Thr Leu Ala Gly Val Thr Val Ala Asn
            340                 345                 350

Pro Ala Arg Phe Leu Ser Pro Thr Val Arg Ala Val Thr Arg Ser
            355                 360                 365
```

```
Glu Thr Ser Arg Pro Ala Ala Pro Ile Pro Arg Gln Asp Thr Glu Arg
        370                 375                 380

<210> SEQ ID NO 4
<211> LENGTH: 384
<212> TYPE: PRT
<213> ORGANISM: Artificial Sequence
<220> FEATURE:
<223> OTHER INFORMATION: Mutant of OpdA

<400> SEQUENCE: 4

Met Gln Thr Arg Arg Asp Ala Leu Lys Ser Ala Ala Ile Thr Leu
1               5                   10                  15

Leu Gly Gly Leu Ala Gly Cys Ala Ser Met Ala Arg Pro Ile Gly Thr
            20                  25                  30

Gly Asp Leu Ile Asn Thr Val Arg Gly Pro Ile Pro Val Ser Glu Ala
            35                  40                  45

Gly Phe Thr Leu Thr His Glu His Ile Cys Gly Ser Ser Ala Gly Phe
    50                  55                  60

Leu Arg Ala Trp Pro Glu Phe Phe Gly Ser Arg Lys Ala Leu Ala Glu
65                  70                  75                  80

Lys Ala Val Arg Gly Leu Arg His Ala Arg Ser Ala Gly Val Gln Thr
                85                  90                  95

Ile Val Asp Val Ser Thr Phe Asp Ile Gly Arg Asp Val Arg Leu Leu
            100                 105                 110

Ala Glu Val Ser Arg Ala Asp Asp Val His Ile Val Ala Ala Thr Gly
            115                 120                 125

Leu Trp Phe Asp Pro Pro Leu Ser Met Arg Met Arg Ser Val Glu Glu
    130                 135                 140

Leu Thr Gln Phe Phe Leu Arg Glu Ile Gln His Gly Ile Glu Asp Thr
145                 150                 155                 160

Gly Ile Arg Ala Gly Ile Ile Lys Val Ala Thr Thr Gly Lys Ala Thr
                165                 170                 175

Pro Phe Gln Glu Leu Val Leu Lys Ala Ala Arg Ala Ser Leu Ala
            180                 185                 190

Thr Gly Val Pro Val Thr Thr His Thr Ser Ala Ser Gln Arg Asp Gly
            195                 200                 205

Glu Gln Gln Ala Ala Ile Phe Glu Ser Glu Gly Leu Ser Pro Ser Arg
    210                 215                 220

Val Cys Ile Gly His Ser Asp Asp Thr Asp Leu Ser Tyr Leu Thr
225                 230                 235                 240

Gly Leu Ala Ala Arg Gly Tyr Leu Val Gly Leu Asp Arg Met Pro Tyr
                245                 250                 255

Ser Ala Ile Gly Leu Glu Gly Asn Ala Ser Ala Leu Ala Leu Phe Gly
            260                 265                 270

Thr Arg Ser Trp Gln Thr Arg Ala Leu Leu Ile Lys Ala Leu Ile Asp
            275                 280                 285

Arg Gly Tyr Lys Asp Arg Ile Leu Val Ser His Asp Trp Leu Phe Gly
    290                 295                 300

Phe Ser Ser Tyr Val Thr Asn Ile Met Asp Val Met Asp Arg Ile Asn
305                 310                 315                 320

Pro Asp Gly Met Ala Phe Val Pro Leu Arg Val Ile Pro Phe Leu Arg
                325                 330                 335

Glu Lys Gly Val Pro Pro Glu Thr Leu Ala Gly Val Thr Val Ala Asn
            340                 345                 350

Pro Ala Arg Phe Leu Ser Pro Thr Val Arg Ala Val Val Thr Arg Ser
```

```
              355                 360                 365
Glu Thr Ser Arg Pro Ala Ala Pro Ile Pro Arg Gln Asp Thr Glu Arg
      370                 375                 380

<210> SEQ ID NO 5
<211> LENGTH: 1155
<212> TYPE: DNA
<213> ORGANISM: Agrobacterium radiobacter

<400> SEQUENCE: 5
atgcaaacga gaagagatgc acttaagtct gcggccgcaa taactctgct cggcggcttg      60
gctgggtgtg caagcatggc ccgaccaatc ggtacaggcg atctgattaa tactgttcgc     120
ggccccattc cagtttcgga agcgggcttc acactgaccc atgagcatat ctgcggcagt     180
tcggcgggat tcctacgtgc gtggccggag tttttcggta gccgcaaagc tctagcggaa     240
aaggctgtga gaggattacg ccatgccaga tcggctggcg tgcaaaccat cgtcgatgtg     300
tcgactttcg atatcggtcg tgacgtccgt ttattggccg aagtttcgcg ggccgccgac     360
gtgcatatcg tggcggcgac tggcttatgg ttcgacccgc cactttcaat gcgaatgcgc     420
agcgtcgaag aactgaccca gttcttcctg cgtgaaatcc aacatggcat cgaagacacc     480
ggtattaggg cgggcattat caaggtcgcg accacaggga aggcgacccc ctttcaagag     540
ttggtgttaa aggcagccgc gcgggccagc ttggccaccg tgttccggt aaccactcac      600 acgtcagcaa gtcagcgcga tggcgagcag caggcagcca tatttgaatc gaaggtttg      660 agcccctcac gggtttgtat cggtcacagc gatgatactg acgatttgag ctacctaacc     720
ggcctcgctg cgcgcggata cctcgtcggt ttagatcgca tgccgtacag tgcgattggt     780
ctagaaggca atgcgagtgc attagcgctc tttggtactc ggtcgtggca aacaagggct     840
ctcttgatca aggcgctcat cgaccgaggc tacaaggatc gaatcctcgt ctcccatgac     900
tggctgttcg ggttttcgag ctatgtcacg aacatcatgg acgtaatgga tcgcataaac     960
ccagatggaa tggccttcgt ccctctgaga gtgatcccat tcctacgaga aagggcgtc     1020 ccgccggaaa cgctagcagg cgtaaccgtg gccaatcccg cgcggttctt gtcaccgacc    1080
gtgcgggccg tcgtgacacg atctgaaact tcccgccctg ccgcgcctat tccccgtcaa    1140
gataccgaac gatga                                                    1155

<210> SEQ ID NO 6
<211> LENGTH: 1071
<212> TYPE: DNA
<213> ORGANISM: Agrobacterium radiobacter

<400> SEQUENCE: 6
ccaatcggta caggcgatct gattaatact gttcgcggcc ccattccagt ttcggaagcg      60
ggcttcacac tgacccatga gcatatctgc ggcagttcgg cgggattcct acgtgcgtgg     120
ccggagtttt tcggtagccg caaagctcta gcggaaaagg ctgtgagagg attacgccat     180
gccagatcgg ctggcgtgca aaccatcgtc gatgtgtcga ctttcgatat cggtcgtgac     240
gtccgtttat tggccgaagt ttcgcgggcc gccgacgtgc atatcgtggc ggcgactggc     300
ttatggttcg acccgccact ttcaatgcga atgcgcagcg tcgaagaact gacccagttc     360
ttcctgcgtg aaatccaaca tggcatcgaa gacaccggta ttagggcggg cattatcaag     420
gtcgcgacca cagggaaggc gaccccctt caagagttgg tgttaaaggc agccgcgcgg     480
gccagcttgg ccaccggtgt tccggtaacc actcacacgt cagcaagtca gcgcgatggc     540
gagcagcagg cagccatatt tgaatccgaa ggtttgagcc cctcacgggt ttgtatcggt     600
```

| | | |
|---|---|---|
| cacagcgatg | atactgacga tttgagctac ctaaccggcc tcgctgcgcg cggatacctc | 660 |
| gtcggtttag | atcgcatgcc gtacagtgcg attggtctag aaggcaatgc gagtgcatta | 720 |
| gcgctctttg | gtactcggtc gtggcaaaca agggctctct tgatcaaggc gctcatcgac | 780 |
| cgaggctaca | aggatcgaat cctcgtctcc catgactggc tgttcgggtt ttcgagctat | 840 |
| gtcacgaaca | tcatggacgt aatggatcgc ataaacccag atggaatggc cttcgtccct | 900 |
| ctgagagtga | tcccattcct acgagagaag ggcgtcccgc cggaaacgct agcaggcgta | 960 |
| accgtggcca | atcccgcgcg gttcttgtca ccgaccgtgc gggccgtcgt gacacgatct | 1020 |
| gaaacttccc | gccctgccgc gcctattccc cgtcaagata ccgaacgatg a | 1071 |

<210> SEQ ID NO 7
<211> LENGTH: 1155
<212> TYPE: DNA
<213> ORGANISM: Artificial Sequence
<220> FEATURE:
<223> OTHER INFORMATION: Mutant of OpdA

<400> SEQUENCE: 7

| | | |
|---|---|---|
| atgcaaacga | gaagagatgc acttaagtct gcggccgcaa taactctgct cggcggcttg | 60 |
| gctgggtgtg | caagcatggc ccgaccaatc ggtacaggcg atctgattaa tactgttcgc | 120 |
| ggctccattc | cagtttcgga agcgggcttc acactgaccc atgagcatat ctgcggcagt | 180 |
| tcggcgggat | tcctacgtgc gtggccggag ttttcggta gccgcaaagc tctagcggaa | 240 |
| aaggctgtga | gaggattacg ccatgccaga tcggctggcg tgcaaaccat cgtcgatgtg | 300 |
| tcgactttcg | atatcggtcg tgacgtccgt ttattggccg aagtttcgcg ggccgccgac | 360 |
| gtgcatatcg | tggcggcgac tggccttatgg ttcgacccgt cactttcaat gcgaatgcgc | 420 |
| agcgtcgaag | aactgaccca gttcttcctg cgtgaaatcc aacatggcat cgaagacacc | 480 |
| ggtattaggg | cggcattat caaggtctcg accacaggga aggcgacccc ctttcaagag | 540 |
| ttggtgttaa | aggcagccgc gcgggccagc ttggccaccg tgttccggt aaccactcac | 600 |
| acgtcagcaa | gtcagcgcga tggcgagcag caggcagcca tatttgaatc cgaaggtttg | 660 |
| agcccctcac | gggtttgtat cggtcacagc gatgatactg acgatttggg ctacctaacc | 720 |
| ggcctcgctg | cgcgcggata cctcgtcggt ttagatcgca tgccgtacag tgcgattggt | 780 |
| ctagaaggca | atgcgagtgc attagcgctc tttggtactc ggtcgtggca aacaagggct | 840 |
| ctcttgatca | aggcgctcat cgaccgaggc tacaaggatc gaatcctcgt ctcccatgac | 900 |
| tggctgttcg | ggttttcgag ctatgtcacg aacatcatgg acgtaatgga tcgcataaac | 960 |
| ccagatggaa | tggccttcgt ccctctgaga gtgatcccat tcctacgaga aagggcgtc | 1020 |
| ccgccggaaa | cgctagcagg cgtaaccgtg gccaatcccg cgcggttctt gtcaccgacc | 1080 |
| gtgcgggccg | tcgtgacacg atctgaaact tcccgccctg ccgcgcctat tccccgtcaa | 1140 |
| gataccgaac | gatga | 1155 |

<210> SEQ ID NO 8
<211> LENGTH: 1155
<212> TYPE: DNA
<213> ORGANISM: Artificial Sequence
<220> FEATURE:
<223> OTHER INFORMATION: Mutant of OpdA

<400> SEQUENCE: 8

| | | |
|---|---|---|
| atgcaaacga | gaagagatgc acttaagtct gcggccgcaa taactctgct cggcggcttg | 60 |
| gctgggtgtg | caagcatggc ccgaccaatc ggtacaggcg atctgattaa tactgttcgc | 120 |

```
ggccccattc cagtttcgga agcgggcttc acactgaccc atgagcatat ctgcggcagt    180
tcggcgggat tcctacgtgc gtggccgag  tttttcggta gccgcaaagc tctagcggaa    240
aaggctgtga gaggattacg ccatgccaga tcggctggcg tgcaaaccat cgtcgatgtg    300
tcgactttcg atatcggtcg tgacgtccgt ttattggccg aagtttcgcg ggccgacgac    360
gtgcatatcg tggcggcgac tggcttatgg ttcgacccgc cactttcaat gcgaatgcgc    420
agcgtcgaag aactgaccca gttcttcctg cgtgaaatcc aacatggcat cgaagacacc    480
ggtattaggg cgggcattat caaggtcgcg accacaggga aggcgacccc ctttcaagag    540
ttggtgttaa aggcagccgc gcgggccagc ttggccaccg tgttccggt  aaccactcac    600 acgtcagcaa gtcagcgcga tggcgagcag caggcagcca tatttgaatc cgaaggtttg    660
agcccctcac gggtttgtat cggtcacagc gatgatactg acgatttgag ctacctaacc    720
ggcctcgctg cgcgcggata cctcgtcggt ttagatcgca tgccgtacag tgcgattggt    780
ctagaaggca atgcgagtgc attagcgctc tttggtactc ggtcgtggca acaagggct    840 ctcttgatca aggcgctcat cgaccgaggc tacaaggatc gaatcctcgt ctcccatgac    900
tggctgttcg ggttttcgag ctatgtcacg aacatcatgg acgtaatgga tcgcataaac    960
ccagatggaa tggccttcgt ccctctgaga gtgatcccat tcctacgaga aagggcgtc    1020 ccgccggaaa cgctagcagg cgtaaccgtg gccaatcccg cgcggttctt gtcaccgacc    1080
gtgcgggccg tcgtgacacg atctgaaact tcccgccctg ccgcgcctat tccccgtcaa    1140
gataccgaac gatga                                                     1155

<210> SEQ ID NO 9
<211> LENGTH: 20
<212> TYPE: DNA
<213> ORGANISM: Artificial Sequence
<220> FEATURE:
<223> OTHER INFORMATION: PCR primer for 16S rRNA gene

<400> SEQUENCE: 9
agagtttgat cmtggctcag                                                 20

<210> SEQ ID NO 10
<211> LENGTH: 22
<212> TYPE: DNA
<213> ORGANISM: Artificial Sequence
<220> FEATURE:
<223> OTHER INFORMATION: PCR primer for 16S rRNA gene

<400> SEQUENCE: 10
tacggytacc ttgttacgac tt                                              22

<210> SEQ ID NO 11
<211> LENGTH: 33
<212> TYPE: DNA
<213> ORGANISM: Artificial Sequence
<220> FEATURE:
<223> OTHER INFORMATION: PCR primer for OpdA gene

<400> SEQUENCE: 11
gatcgtctgc agccaatcgg tacaggcgat ctg                                  33

<210> SEQ ID NO 12
<211> LENGTH: 39
<212> TYPE: DNA
<213> ORGANISM: Artificial Sequence
<220> FEATURE:
<223> OTHER INFORMATION: PCR primer for OpdA gene
```

```
<400> SEQUENCE: 12
gatcgtaagc tttcatcgtt cggtatcttg acggggaat                                  39

<210> SEQ ID NO 13
<211> LENGTH: 33
<212> TYPE: DNA
<213> ORGANISM: Artificial Sequence
<220> FEATURE:
<223> OTHER INFORMATION: PCR primer for OpdA gene

<400> SEQUENCE: 13
gatcgtggat cctcgatcgg cacaggcgat cgg                                        33

<210> SEQ ID NO 14
<211> LENGTH: 33
<212> TYPE: DNA
<213> ORGANISM: Artificial Sequence
<220> FEATURE:
<223> OTHER INFORMATION: PCR primer for OpdA gene

<400> SEQUENCE: 14
gatcgtaagc tttcatgacg cccgcaaggt cgg                                        33

<210> SEQ ID NO 15
<211> LENGTH: 30
<212> TYPE: DNA
<213> ORGANISM: Artificial Sequence
<220> FEATURE:
<223> OTHER INFORMATION: PCR primer

<400> SEQUENCE: 15
gatcgtgaat tccatatgcc aatcggtaca                                            30

<210> SEQ ID NO 16
<211> LENGTH: 30
<212> TYPE: DNA
<213> ORGANISM: Artificial Sequence
<220> FEATURE:
<223> OTHER INFORMATION: PCR primer

<400> SEQUENCE: 16
gatcgtggat cctcatcgtt cggtatcttg                                            30

<210> SEQ ID NO 17
<211> LENGTH: 365
<212> TYPE: PRT
<213> ORGANISM: Flavobacterium sp.

<400> SEQUENCE: 17

Met Gln Thr Arg Arg Val Val Leu Lys Ser Ala Ala Ala Gly Thr
1               5                   10                  15

Leu Leu Gly Gly Leu Ala Gly Cys Ala Ser Val Ala Gly Ser Ile Gly
                20                  25                  30

Thr Gly Asp Arg Ile Asn Thr Val Arg Gly Pro Ile Thr Ile Ser Glu
            35                  40                  45

Ala Gly Phe Thr Leu Thr His Glu His Ile Cys Gly Ser Ser Ala Gly
    50                  55                  60

Phe Leu Arg Ala Trp Pro Glu Phe Phe Gly Ser Arg Lys Ala Leu Ala
65                  70                  75                  80

Glu Lys Ala Val Arg Gly Leu Arg Arg Ala Arg Ala Ala Gly Val Arg
                85                  90                  95

Thr Ile Val Asp Val Ser Thr Phe Asp Ile Gly Arg Asp Val Ser Leu
```

-continued

```
                        100                 105                 110
Leu Ala Glu Val Ser Arg Ala Ala Asp Val His Ile Val Ala Ala Thr
                115                 120                 125

Gly Leu Trp Phe Asp Pro Pro Leu Ser Met Arg Leu Arg Ser Val Glu
            130                 135                 140

Glu Leu Thr Gln Phe Phe Leu Arg Glu Ile Gln Tyr Gly Ile Glu Asp
145                 150                 155                 160

Thr Gly Ile Arg Ala Gly Ile Ile Lys Val Ala Thr Thr Gly Lys Ala
                165                 170                 175

Thr Pro Phe Gln Glu Leu Val Leu Lys Ala Ala Arg Ala Ser Leu
                180                 185                 190

Ala Thr Gly Val Pro Val Thr Thr His Thr Ala Ala Ser Gln Arg Asp
                195                 200                 205

Gly Glu Gln Gln Ala Ala Ile Phe Glu Ser Glu Gly Leu Ser Pro Ser
            210                 215                 220

Arg Val Cys Ile Gly His Ser Asp Asp Thr Asp Asp Leu Ser Tyr Leu
225                 230                 235                 240

Thr Ala Leu Ala Ala Arg Gly Tyr Leu Ile Gly Leu Asp His Ile Pro
                245                 250                 255

His Ser Ala Ile Gly Leu Glu Asp Asn Ala Ser Ala Ser Ala Leu Leu
                260                 265                 270

Gly Ile Arg Ser Trp Gln Thr Arg Ala Leu Leu Ile Lys Ala Leu Ile
                275                 280                 285

Asp Gln Gly Tyr Met Lys Gln Ile Leu Val Ser Asn Asp Trp Leu Phe
            290                 295                 300

Gly Phe Ser Ser Tyr Val Thr Asn Ile Met Asp Val Met Asp Arg Val
305                 310                 315                 320

Asn Pro Asp Gly Met Ala Phe Ile Pro Leu Arg Val Ile Pro Phe Leu
                325                 330                 335

Arg Glu Lys Gly Val Pro Gln Glu Thr Leu Ala Gly Ile Thr Val Thr
                340                 345                 350

Asn Pro Ala Arg Phe Leu Ser Pro Thr Leu Arg Ala Ser
                355                 360                 365
```